United States Patent
Liao et al.

(10) Patent No.: US 9,550,980 B2
(45) Date of Patent: Jan. 24, 2017

(54) COMPOSITION AND METHODS FOR THE PRODUCTION OF L-HOMOALANINE

(71) Applicant: The Regents of the University of California, Oakland, CA (US)

(72) Inventors: James C. Liao, Los Angeles, CA (US); Kechun Zhang, Minneapolis, MN (US); Kwang Myung Cho, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/879,914

(22) Filed: Oct. 9, 2015

(65) Prior Publication Data

US 2016/0053236 A1    Feb. 25, 2016

Related U.S. Application Data

(62) Division of application No. 13/581,287, filed as application No. PCT/US2011/023615 on Feb. 25, 2011, now Pat. No. 9,187,774.

(60) Provisional application No. 61/308,746, filed on Feb. 26, 2010.

(51) Int. Cl.
| | |
|---|---|
| *C12N 9/02* | (2006.01) |
| *C12N 15/00* | (2006.01) |
| *C12N 9/06* | (2006.01) |
| *C12P 13/04* | (2006.01) |
| *C12P 13/06* | (2006.01) |

(52) U.S. Cl.
CPC ............. *C12N 9/0016* (2013.01); *C12P 13/04* (2013.01); *C12P 13/06* (2013.01); *C12Y 104/01002* (2013.01); *Y02P 20/52* (2015.11)

(58) Field of Classification Search
CPC ..................... C12N 9/0016; C12Y 104/01002; C12Y 104/01003; C12Y 104/01004; C12P 13/04

See application file for complete search history.

(56) References Cited

U.S. PATENT DOCUMENTS

2007/0009995 A1    1/2007 Bogosian et al.

FOREIGN PATENT DOCUMENTS

WO        2005/038017        4/2005

OTHER PUBLICATIONS

Ford et al., Prot. Express. Purif. 2:95-107, 1991.*
Ausubel et al., "Current Protocols in Molecular Biology", Supplement 59, Section I, pp. 1.1.1-1.1.7, 2002.*
Khan, et al., Molecular Properties and Enhancement of Thermostability by Random Mutagenesis of Glutamate Dehydrogenase from Bacillus Subtillis, Biosci Biotechnol Biochem, 2005, 69(10) 1861-1870.
Leuchtenberger, W., et al., "Biotechnological production of amino acids and derivatives: current status and prospects", Appl. Microbiol. Biotechnol., 2005, 69: 1-8.
Wang, X.G., et al., "Conversion of a glutamate dehydrogenase into methionine/norleucine dehydrogenase by site-directed mutagenesis", Eur. J. Biochem., 268, 5791-5799, 2001.
Chinese Search Report dated Sep. 16, 2013, CN Application No. 201180021223.0.
European Search Report dated Aug. 20, 2013, EP Application No. 11748179.6.
PCT International Search Report and Written Opinion dated Aug. 17, 2011, International Application No. PCT/US2011/026315.
Fotheringham, I. G., et al., "Engineering of a Novel Biochemical Pathway for the Biosynthesis of L-2-aminobutyric Acid in *Escherichia coli* K12", Bioorganic & Medicinal Chemistry 7 (1999), pp. 2209-2213, abstract.
McPherson, M. J., et al., "Multiple interactions of lysine-128 of *Escherichia coli* glutamate dehydrogenase revealed by site-directed mutagenesis studies", Protein Engineering, 1998, vol. 2, No. 2, pp. 147-152.
Zhang, K., et al., "Expanding metabolism for total biosynthesis of the nonnatural amino acid L-homoalanine", Proc. Natl Acad Sci (PNAS) Mar. 23, 2010, 107(14), pp. 6234-6239.

* cited by examiner

*Primary Examiner* — David J Steadman
(74) *Attorney, Agent, or Firm* — Gates & Cooper LLP

(57) ABSTRACT

Healthcare costs are a significant worldwide, with many patients being denied medications because of their high prices. One approach to addressing this problem involves the biosynthesis of chiral drug intermediates, an environmentally friendly solution that can be used to generate pharmaceuticals at much lower costs than conventional techniques. In this context, embodiments of the invention comprise methods and materials designed to allow microorganisms to biosynthesize the nonnatural amino acid L-homoalanine. As is known in the art, L-homoalanine is a chiral precursor of a variety of pharmaceutically valuable compounds including the anticonvulsant medications levetiracetam (sold under the trade name Keppra®) and brivaracetam, as well as ethambutol, a bacteriostatic antimycobacterial drug used to treat tuberculosis. Consequently, embodiments of the invention can be used in low cost, environmentally friendly processes to generate these and other valuable compounds.

20 Claims, 17 Drawing Sheets

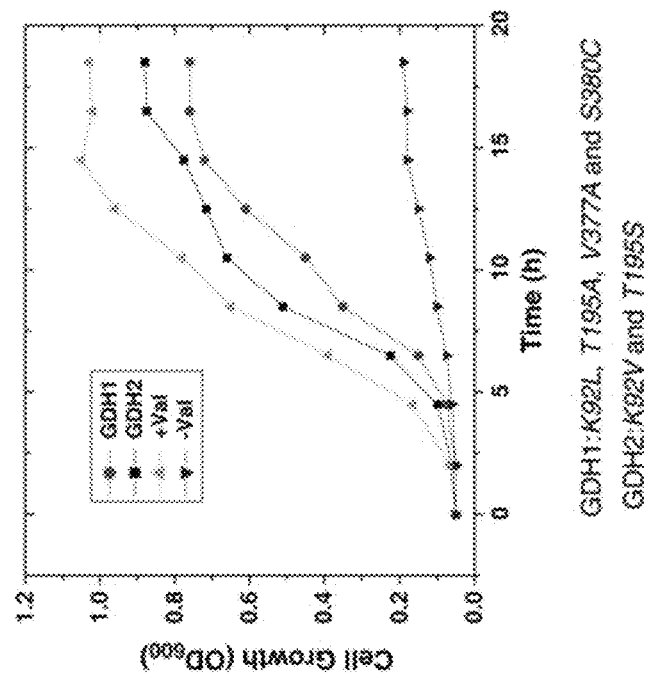
FIG. 4C
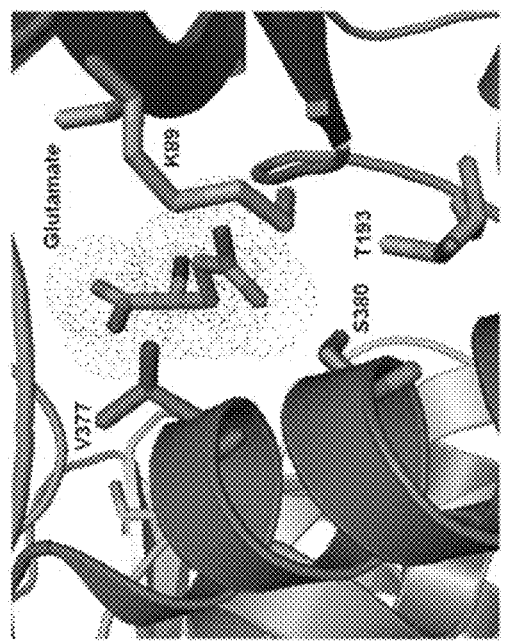
FIG. 4A
FIG. 4B

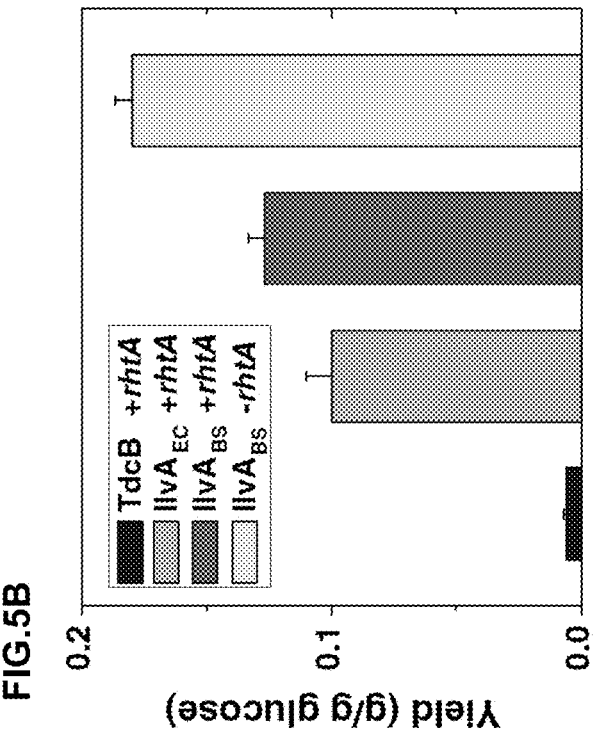
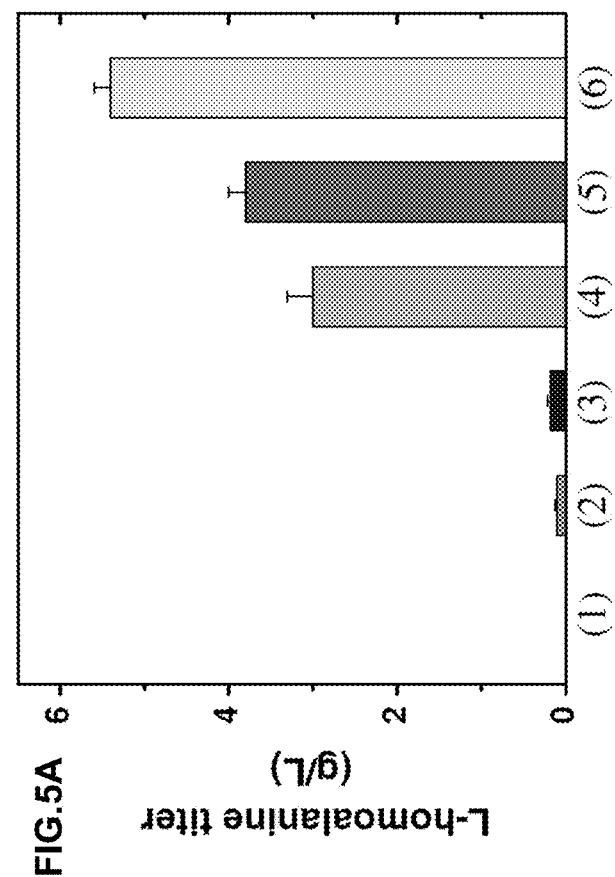
FIG.5A
FIG.5B

| Substrate | Structure | GDHwt $K_m$ (mM) | GDHwt $k_{cat}$ (s$^{-1}$) | GDHwt $k_{cat}/K_m$ (mM$^{-1}$ s$^{-1}$) | GDH2 $K_m$ (mM) | GDH2 $k_{cat}$ (s$^{-1}$) | GDH2 $k_{cat}/K_m$ (mM$^{-1}$ s$^{-1}$) |
|---|---|---|---|---|---|---|---|
| 2-ketoglutarate | 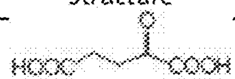 | 0.30 ± 0.02 | 187.2 ± 8.4 | 624 | 69.2 ± 4.9 | 14.0 ± 0.6 | 0.2 |
| 2-Ketoisovalerate | 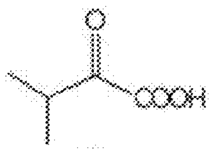 | 152.7 ± 9.5 | 10.4 ± 0.7 | 0.07 | 145.6 ± 6.5 | 47.1 ± 4.5 | 0.3 |
| 2-ketobutyrate | 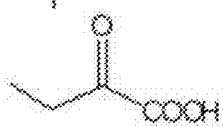 | 35.4 ± 7.4 | 47.2 ± 5.0 | 1.3 | 8.4 ± 1.7 | 90.2 ± 5.4 | 10.7 |

FIG. 6

| IlvEaccfwd | GCATACGGTACC ATGACCACGAAGAAAGCTGATTACATTTG (SEQ ID NO: 8) |
|---|---|
| IlvExabrev | GCATACTCTAGA TTATTGATTAACTTGATCTAACCAGCCCCAT (SEQ ID NO: 9) |
| Vdhsaaccfwd | GCATACGGTACC ATGACCGATGTATCCGACGGCGT (SEQ ID NO: 10) |
| Vdhsaxbarev | GCATACTCTAGA TTAGCCCCGGCGGGCCTCCGCCATG (SEQ ID NO: 11) |
| Vdhscaccfwd | GCATACGGTACC ATGACCGACGTAAACGGCGCACC (SEQ ID NO: 12) |
| Vdhscxbarev | GCATACTCTAGA TTACGGCCGGGGACGGGCCTCCGCCATC (SEQ ID NO: 13) |
| Vdhsfaccfwd | GCATACGGTACC ATGACCGACGCGTCCCACCCCAC (SEQ ID NO: 14) |
| Vdhsfxbarev | GCATACTCTAGA TTAGACGGTGCGGGCCTCCGCCATG (SEQ ID NO: 15) |
| GDHccaccfwd | GCATACGGTACC ATGGATCAGACATATTCTCTGGAGTCATTC (SEQ ID NO: 16) |
| GDHecxabrev | GCATACTCTAGA TTAAATCACACCCTGCGCCAGC (SEQ ID NO: 17) |
| GDH_k92lib | GCTCTGCCATCGGCCCGTACNNKGGCGGTATGCGCTTCCATCCG (SEQ ID NO: 18) |
| GDH_k92lib_rev | CGGATGGAAGCGCATACCGCCMNNGTACGGGCCGATGGCAGAGC (SEQ ID NO: 19) |
| GDH_T195lib | CAACAATACCGCCTGCGTCTTCNNKGGTAAGGGCCTTTCATTTGG (SEQ ID NO: 20) |
| GDH_T195lib_rev | CCAAATGAAAGGCCCTTACCMNNGAAGACGCAGGCGGTATTGTTG (SEQ ID NO: 21) |
| GDH_VSlib | GTAAAGCGGCTAATGCTGGTGGCNNKGCTACANNKGGCCTGGAAATGGCACAAAAC (SEQ ID NO: 22) |
| GDH_VSlib_rev | GTTTTGTGCCATTTCCAGGCCMNNTGTAGCMNNGCCACCAGCATTAGCCGCTTTAC (SEQ ID NO: 23) |
| GDHecsalfwd | GCATAC GTCGAC AAGAGGAGAAAGTTACC ATGGATCAGACATATTCTCTGGAGTCATTC (SEQ ID NO: 24) |
| TdcBaccfwd | GCATAC GGTACC ATGCATATTACATACGATCTGCCGGTTG (SEQ ID NO: 25) |
| TdcBsalrev | GCATAC GTCGAC TTAAGCGTCAACGAAACCGGTGATTTG (SEQ ID NO: 26) |
| IlvAecaccfwd | GCATACGGTACC ATGGCTGACTCGCAACCCCTG (SEQ ID NO: 27) |
| IlvAecsalrev | GCATAC GTCGAC CTAACCCGCCAAAAAGAACCTGA (SEQ ID NO: 28) |
| IlvAbsaccfwd | GCATACGGTACC ATGAAACCGTTGCTTAAAGAAAACTCTCTC (SEQ ID NO: 29) |
| IlvAbssalrev | GCATAC GTCGAC TTAGATTAGCAAATGGAACAAGTCCTCATCC (SEQ ID NO: 30) |
| GDHbamfwd | GCATAC GGATCC ATGGATCAGACATATTCTCTGGAGTCATTC (SEQ ID NO: 31) |
| GDHbamrev | GCATAC GGATCC TTAAATCACACCCTGCGCCAGC (SEQ ID NO: 32) |

| matrix B | "-V$_{in}$" |
|---|---|
| Glucose | -1.000 |
| G6P | 0.000 |
| F6P | 0.000 |
| F16BP | 0.000 |
| GA3P | 0.000 |
| PEP | 0.000 |
| Pyr | 0.000 |
| 6PG | 0.000 |
| R5P | 0.000 |
| OAA | 0.000 |
| ASP | 0.000 |
| THR | 0.000 |
| AceCoA | 0.000 |
| CoASH | 0.000 |
| Citrate | 0.000 |
| GA | 0.000 |
| 2KG | 0.000 |
| SucCoA | 0.000 |
| Succinate | 0.000 |
| Fumarate | 0.000 |
| Malate | 0.000 |
| CO2 | 0.000 |
| NADH | 0.000 |
| NADPH | 0.000 |
| ATP | 0.000 |

FIG. 11

| Pathway | Flux | f |
|---|---|---|
| Glucose uptake (PTS) | v1 | 0.000 |
| Glycolysis | v2 | 0.000 |
| | v3 | 0.000 |
| | v4 | 0.000 |
| | v5 | 0.000 |
| | v6 | 0.000 |
| ppc | v7 | 0.000 |
| V OAA-->ASP | v8 | 0.000 |
| v ASP-->THR | v9 | 0.000 |
| v THR-->HA | v10 | -1.000 |
| v Pyr-->AceCoA | v11 | 0.000 |
| TCA | v12 | 0.000 |
| | v13 | 0.000 |
| | v14 | 0.000 |
| | v15 | 0.000 |
| | v16 | 0.000 |
| | v17 | 0.000 |
| | v18 | 0.000 |
| v 2KG-->Glu | v19 | 0.000 |
| PPP | v20 | 0.000 |
| | v21 | 0.000 |
| | v22 | 0.000 |
| | VNADH-out | 0.000 |
| | VNADPH-out | 0.000 |
| | VATP-out | 0.000 |
| | VCO2-out | 0.000 |
| | Vpps | 0.000 |
| | VNADH-NADPH | 0.000 |
| | VNADH-ATP | 0.000 |
| | VNADPH-ATP | 0.000 |

FIG. 12

Summary of the theoretical yield for homoalanine production from glucose

| Transhydrogenase (NADH→NADPH) | ATP/NAD(P)H | Theoretical Yield | |
|---|---|---|---|
| | | Molar Yield (mol/mol) | Mass Yield (g/g) |
| YES | 1.5 | 1.188 | 0.68 |
| YES | 2.0 | 1.200 | 0.69 |
| YES | 3.0 | 1.226 | 0.70 |
| NO | 1.5~3.0 | 0.733 | 0.42 |

FIG. 13

* Assumption: 1) Energy production from UQH2 derived from succinate dehydrogenase in TCA cycle was not included. 2) Non-oxidative branch of Pentose Phosphate Pathway was assumed 3R5P→2F6P+GA3P

COMPOSITION AND METHODS FOR THE PRODUCTION OF L-HOMOALANINE

CROSS REFERENCE TO RELATED APPLICATIONS

This application is a divisional application that claims the benefit under 35 U.S.C. §121 of U.S. patent application Ser. No. 13/581,287, filed Aug. 24, 2012, titled "Compositions and Methods for the Production of L-Homoalanine", which claims priority under Section 119(e) from U.S. provisional patent application No. 61/308,746, filed Feb. 26, 2010, the entire contents of which are incorporated herein by reference.

FIELD OF THE INVENTION

The invention provides methods and materials for synthesizing compounds such as L-homoalanine including procedures using microbial hosts and recombinant molecules.

BACKGROUND OF THE INVENTION

The dramatic increase in healthcare costs has become a significant burden to the world, with many patients being denied medications because of their high prices. The biosynthesis of chiral drugs and drug intermediates offers an environmentally friendly approach to addressing such problems, for example, by providing cost effective methodologies for the production of therapeutic agents as well as the intermediates and/or precursors used to make such agents.

L-homoalanine is a nonnatural amino acid that is a key chiral intermediate for the synthesis of several important drugs (FIG. 1A). For example, it can be converted to S-2-aminobutyramide, which is the immediate precursor of the antiepileptic drugs levetiracetam and brivaracetam. L-homoalanine can also be converted to S-2-aminobutanol, a chemical intermediate in methods for synthesizing the antituberculosis compound ethambutol. Methods for synthesizing therapeutic compounds such as levetiracetam and ethambutol must overcome a number of technical challenges. For example, the optical purity of these drugs is critical for therapeutic safety and efficacy. The R-enantiomer of levetiracetam has no antiepileptic activity (see, e.g. Shorvon et al., (2002) Journal of Neurology, Neurosurgery, and Psychiatry 72(4):426-429) and (R,R)-form of ethambutol can cause blindness (see, e.g. Breuer M, et al. (2004) Angewandte Chemie International Edition 43(7):788-824).

Even though ethambutol and levetiracetam are now generic drugs, in many countries the cost of just one month's supply exceeds the entire annual per capita health expenditure (see, e.g. Moore-Gillon J (2001) Ann NY Acad Sci 953:233-240). The prohibitive drug price has created global healthcare problems. For example, while epilepsy affects over 50 million people worldwide, most of the patients cannot afford the levetiracetam treatment, and must use cheaper but much less effective alternatives such as phenobarbital (see, e.g. Scott et al. (2001) B World Health Organ 79:344-351). One approach to reducing drug costs in order to make them more widely available involves cost-effective approaches to L-homoalanine synthesis (e.g. by reducing the manufacturing cost of compounds such as levetiracetam).

Most of the natural L-amino acids can now be produced from glucose by microbial fermentation (see, e.g. Ikeda M (2002) Adv Biochem Eng Biot 79:1-35). Notably, L-glutamate, L-lysine, and L-threonine are produced more than 2 million tons annually (see, e.g. Leuchtenberger et al. (2005) Appl Microbiol Biotechnol 69(1):1-8). In contrast to methods for making natural L-amino acids, methods for the commercial-scale preparation of nonnatural amino acids are typically complex as well as environmentally unfriendly. In one prior art approach, chemically synthesized 2-ketoacids are asymmetrically converted to optically pure nonnatural amino acids by transaminases or dehydrognenases (see, e.g. Leuchtenberger et al. (2005) Appl Microbiol Biotechnol 69(1):1-8; Taylor et al. (1998) Trends Biotechnol 16(10): 412-418). Another approach uses enzymes such as acylases or amidases to resolve racemic mixtures of nonnatural amino acids (see, e.g. Leuchtenberger et al. (2005) Appl Microbiol Biotechnol 69(1):1-8).

Due to, for example, their usefulness in a making a variety of valuable therapeutic compounds, there is a need in the art for methods and materials that facilitate the cost effective and environmentally friendly biosynthesis of nonnatural amino acids such as L-homoalanine. Unlike natural amino acids however, the total biosynthesis of nonnatural amino acids from simple sugars involves significant technical challenges. For example, in one environmentally friendly and cost effective approach, metabolic pathways in an organism are altered in order to expand the biosynthetic capabilities of that organism (see, e.g. Zhang et al. (2008) Proc Natl Acad Sci USA 105(52):20653-20658). In such approaches, the altered metabolic pathways then facilitate or direct the production of a target compound such as a nonnatural amino acid (see, e.g. Causey et al. (2003) Proc Natl Acad Sci USA 100(3):825-832). Unfortunately, however, the results of any manipulation designed to alter an organism's metabolic pathways can be unpredictable and such efforts typically require extensive protein evolution (see, e.g. Arnold F H (2001) Nature 409(6817):253-257).

SUMMARY OF THE INVENTION

Embodiments of the invention disclosed herein provide methods and materials for biosynthesizing the nonnatural amino acid L-homoalanine. L-homoalanine is a chiral precursor of a variety of pharmaceutically valuable compounds including the anticonvulsant medications levetiracetam and brivaracetam, as well as ethambutol, a bacteriostatic antimycobacterial drug used to treat tuberculosis. Embodiments of the invention include compositions of matter comprising modified polypeptides and/or microorganisms and/or L-homoalanine.

As illustrated in the Examples below, a selection strategy was used to generate recombinant glutamate dehydrogenase ("GDH") polypeptides. These recombinant polypeptides exhibit properties that facilitate their use in the production of L-homoalanine, for example a specificity constant $k_{cat}/K_m$ towards 2-ketobutyrate is 50-fold higher than the specificity constant towards 2-ketoglutarate, the natural substrate. The recombinant glutamate dehydrogenase polypeptides disclosed herein can be used in methods for the cost effective synthesis of L-homoalanine in commercially significant quantities. In one illustrative embodiment of the invention, the expression of a recombinant glutamate dehydrogenase in combination with a *Bacillus subtilis* threonine dehydratase protein in a threonine-hyperproducing *Escherichia coli* strain (ATCC98082, ΔrhtA) is shown to produce 5.4 g/L L-homoalanine from 30 WL glucose (0.18 g/g glucose yield, 26% of the theoretical maximum).

The invention disclosed herein has a number of embodiments. Illustrative embodiments include glutamate dehydrogenase polypeptides having a specificity constant $k_{cat}/K_m$ for 2-ketobutyrate that is greater than their specificity constant for 2-ketoglutarate. A typical embodiment of the invention is a composition of matter comprising a glutamate dehydrogenase polypeptide having an at least 95% identity to SEQ ID NO: 1, and further comprising an amino acid substitution mutation at residue position K92 and/or T195 (for example K92V and T195S). In certain embodiments of the invention, the glutamate dehydrogenase polypeptide further comprises at least 2-10 substitution, deletion or insertion mutations as compared to the wild type glutamate dehydrogenase polypeptide of SEQ ID NO: 1. Optionally for example, the glutamate dehydrogenase polypeptide includes at least one amino acid substitution mutation comprising K92L, K92V, T195S, T195A, V377A or S380C. A related embodiment of the invention is an isolated glutamate dehydrogenase polynucleotide having an at least 95% identity to SEQ ID NO: 2 and encoding a glutamate dehydrogenase polypeptide that comprises at least one mutation at amino acid position K92, T195, V377 or S380; and further exhibits a specificity for 2-ketobutyrate that is greater than its specificity for 2-ketoglutarate.

Embodiments of the invention include compositions comprising a glutamate dehydrogenase polypeptide disclosed herein in combination with an organism such as *Escherichia coli* or *Corynebacterium glutamicum*. In typical embodiments, the *Escherichia coli* or *Corynebacterium glutamicum* organisms have been transformed with an expression vector encoding a glutamate dehydrogenase polypeptide disclosed herein. In certain embodiments of the invention, the organism is a strain of *Escherichia coli* that produces relatively high levels of threonine, for example one that can produce at least 2, 3, 4, 5, 6, 7 or 8 g/L threonine from 30 g/L glucose in a nutrient media. In some embodiments of the invention the organism is selected to have a mutation in one or more genes in a metabolic pathway, for example a strain of *Escherichia coli* that comprises a mutation in a rhtA polypeptide of SEQ ID NO: 5 that results in a decreased threonine export activity as compared to wild type rhtA polypeptide. In some embodiments of the invention, the organism further overexpresses one or more polypeptides in combination with the glutamate dehydrogenase polypeptides disclosed herein. In one illustrative embodiment, the organism has been transformed with an expression vector encoding a GDH as disclosed herein as well an expression vector encoding a threonine dehydratase polypeptide having an at least 95% identity to SEQ ID NO: 6 or SEQ ID NO: 7. In other embodiments of the invention, the genes for multiple polypeptides used to alter an organism metabolic pathways are encoded on a single expression vector. Optionally, the organism can synthesize L-homoalanine at a concentration of at least 1, 2, 3, 4 or 5 g/L in a nutrient media.

Embodiments of the invention include methods for making L-homoalanine. One illustrative embodiment of the invention is a method for making L-homoalanine comprising: placing an *Escherichia coli* or *Corynebacterium glutamicum* organism into a nutrient medium, wherein the organism comprises a glutamate dehydrogenase polypeptide having an at least 95% identity to SEQ ID NO: 1 and an amino acid substitution mutation at residue position K92 or T195. This organism is then cultured in a nutrient medium under conditions that allows it to biosynthesize L-homoalanine. Typically the glutamate dehydrogenase polypeptide used in such methods further comprises at least 2-10 substitution, deletion or insertion mutations as compared to the wild type glutamate dehydrogenase polypeptide of SEQ ID NO: 1. In certain embodiments of the invention, the organism is *Escherichia coli* comprising a mutation in a rhtA polypeptide of SEQ ID NO: 5 that results in a decreased threonine export activity as compared to wild type rhtA polypeptide. In certain embodiments of the invention, the organism is transformed with an expression vector encoding a threonine dehydratase polypeptide having an at least 95% identity to SEQ ID NO: 6 or SEQ ID NO: 7.

In typical embodiments of the invention, the organism is grown under at least one of the following conditions: at a temperature between 30-40° C.; for a time period between at least 4 to at least 48 hours; at a pH between 6-8; and/or in a nutrient media comprising, for example, M9, LB, F1 or TB media. In one illustrative embodiment, the nutrient medium comprises M9 medium; and the organism is a strain of *Escherichia coli* selected for its ability to make at least 2, 3, 4, 5, 6, 7 or 8 g/L threonine from 30 g/L glucose in the M9 medium. Typically in these methods, the organism can make L-homoalanine at a concentration of at least 1, 2, 3, 4 or 5 g/L in a nutrient medium.

Certain embodiments of the methods for making L-homoalanine include further steps to purify and/or chemically modify a L-homoalanine composition disclosed herein. For example, some embodiments of the invention include at least one purification step comprising lysis of cells of an isolated organism used to make L-homoalanine (e.g. organism within a nutrient media). Other embodiments of the invention can also include at least one purification step comprising centrifugation of cells or cell lysates of an isolated organism used to make L-homoalanine. Other embodiments can include at least one purification step comprising precipitation of one or more compounds present in a medium used to make L-homoalanine (e.g. L-homoalanine itself). Embodiments can include at least one purification step comprising the filtration and/or the concentration of one or more compounds present in a nutrient media (e.g. L-homoalanine). Embodiments can include at least one purification step comprising a chromatographic separation of one or more compounds present in a nutrient media (e.g. L-homoalanine). Related embodiments of the invention include further methodological steps in which a L-homoalanine composition made according to an embodiment of the invention is chemically modified by, for example, performing an chemical reaction such as an amidation or reduction reaction on the L-homoalanine in order to generate further compounds such as S-2-aminobutyramide, S-2-aminobutanol, levetiracetam, brivaracetam or ethambutol.

Embodiments of the invention also include articles of manufacture and/or kits designed to facilitate the methods of the invention. Typically such kits include instructions for using the elements therein according to the methods of the present invention. Such kits can comprise a carrier means being compartmentalized to receive in close confinement one or more container means such as vials, tubes, and the like, each of the container means comprising one of the separate elements to be used in the method. One of the containers can comprise a vial, for example, containing an expression vector encoding a polypeptide disclosed herein, for example one encoding a glutamate dehydrogenase polypeptide having an altered substrate specificity. Optionally the expression vector has been transformed into an organism such as *Escherichia coli* or *Corynebacterium glutamicum* in order to facilitate their production of L-homoalanine. One illustrative embodiment of the invention is a kit for synthesizing L-homoalanine, the kit comprising: an expression vector encoding a glutamate dehydrogenase polypeptide having an at least 95% identity to SEQ ID NO: 1 and an amino acid substitution mutation at residue position K92 or T195. Typically the kit includes a container for this expression vector. Optionally the kit further comprises an expression vector encoding a threonine dehydratase polypeptide having an at least 95% identity to SEQ ID NO: 6 or SEQ ID NO: 7 and/or a live *Escherichia coli* strain (e.g. a strain of *Escherichia coli* overexpresses threonine and/or one that comprises a mutation in a rhtA polypeptide of SEQ ID NO: 5 resulting in a decreased threonine export activity as compared to wild type rhtA polypeptide).

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE DRAWINGS

FIG. 1 shows illustrative pathways and processes for the synthesis of L-homoalanine and related compounds.

FIG. 3 illustrates a selection strategy to evolve glutamate dehydrogenase (GDH) for amination of 2-ketobutyrate.

FIG. 4 shows a construction of a GDH library for evolution. FIG. 4A illustrates a binding pocket of *Clostridium symbiosum* glutamate dehydrogenase (PDB: 1BGV) complexed with its natural substrate glutamate. Residues K89, T193, V377, and S380 are within a radius of 6 Å of the γ-carbon of glutamate. FIG. 4B shows the sequence alignment of *C. symbiosum* and *E. coli* GDH. The binding pocket is conserved, and the corresponding residues of *E. coli* GDH are K92, T195, V377, and S380. These residues were subjected to site-saturation mutagenesis with randomized NNK codon. A library size of 2 million members was transformed into valine auxotrophic *E. coli* and selected for mutants growing in M9 minimal medium. FIG. 4C is a graph showing the growth curve of *E. coli* (AavtA, AilvE) transformants in minimal medium. −Val means absence of valine. +Val means presence of valine. Or cells are transformed with GDH1 (K92L, T195A, V377A, and S380C mutations) or GDH2 (K92V and T195S mutations) mutant. Cells did not grow up in absence of valine in the minimal medium, while GDH mutants could rescue cell growth without valine addition.

FIG. 5 shows graphs illustrating the production of L-homoalanine with different combinations of *E. coli* strains and threonine dehydratases. FIG. 5A is a graph with horizontal axis labels defined as follows: (1) BW25113; (2) BW25113 with overexpression of GDH2; (3) ATCC98082 with overexpression of TdcB & GDH2; (4) ATCC98082 with overexpression of IlvAEc & GDH2; (5) ATCC98082 with overexpression of IlvA$_{BS}$ & GDH2; and (6) ATCC98082 (ArhtA) with overexpression of IlvA$_{BS}$ and GDH2. FIG. 5B is a graph showing the yield of L-homoalanine biosynthesis from glucose. The error bars represent standard deviations from three independent experiments.

FIG. 6 is a table illustrating the kinetic parameters of wild type and mutant glutamate dehydrogenases.

FIG. 7 is a table illustrating the synthetic oligonucleotides for plasmid construction.

FIG. 10 illustrates a stoichiometric matrix A. Matrix A is the stoichiometric matrix and V is the vector of flux in each reaction included. The rows of matrix A correspond to each metabolite, and the columns of matrix A correspond to each reaction (or lumped reaction) considered.

FIG. 11 illustrates a vector matrix B. Matrix B is a vector consisting of negative glucose input and zeros. The rows of matrix B correspond to each metabolite.

FIG. 12 is a table illustrating the f vector and the definition of fluxes. f vector is defined to fit the formalism, $$\min_x f^T x$$

such that $A_{eq}x = b_{eq}$.

FIG. 13 is a table summarizing the theoretical yield for homoalanine production from glucose. The table shows the results of the maximum theoretical yield for various combination of the two variations. It is assumed that: 1) energy production from UQH2 derived from succinate dehydrogenase in TCA cycle was not included; and 2) non-oxidative branch of Pentose Phosphate Pathway was assumed 3R5P→2F6P+GA3P.

Figure 14:
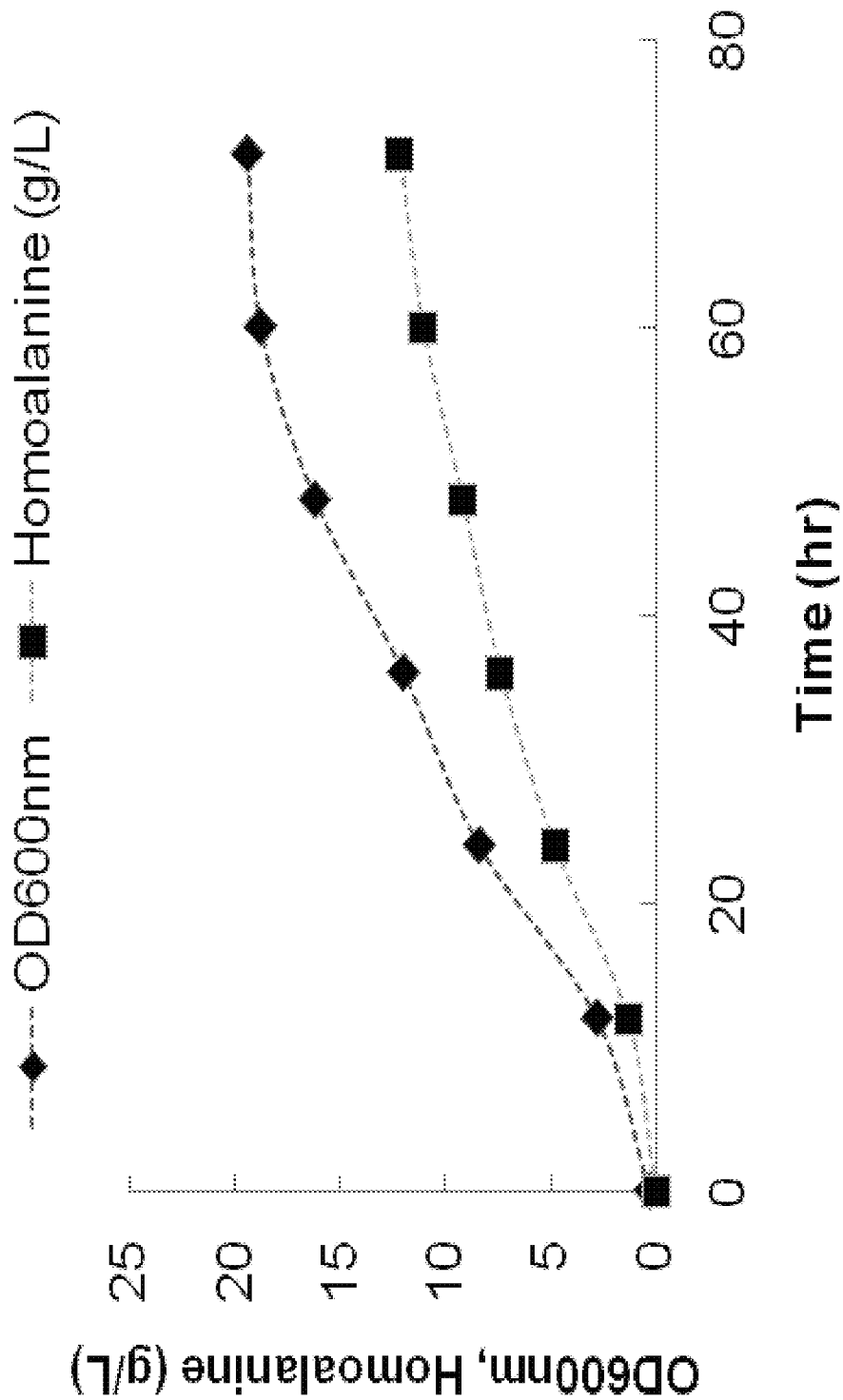

FIG. 14 is a graph illustrating the production of L-Homoalanine in a fermentor (5 L).

Figure 15:
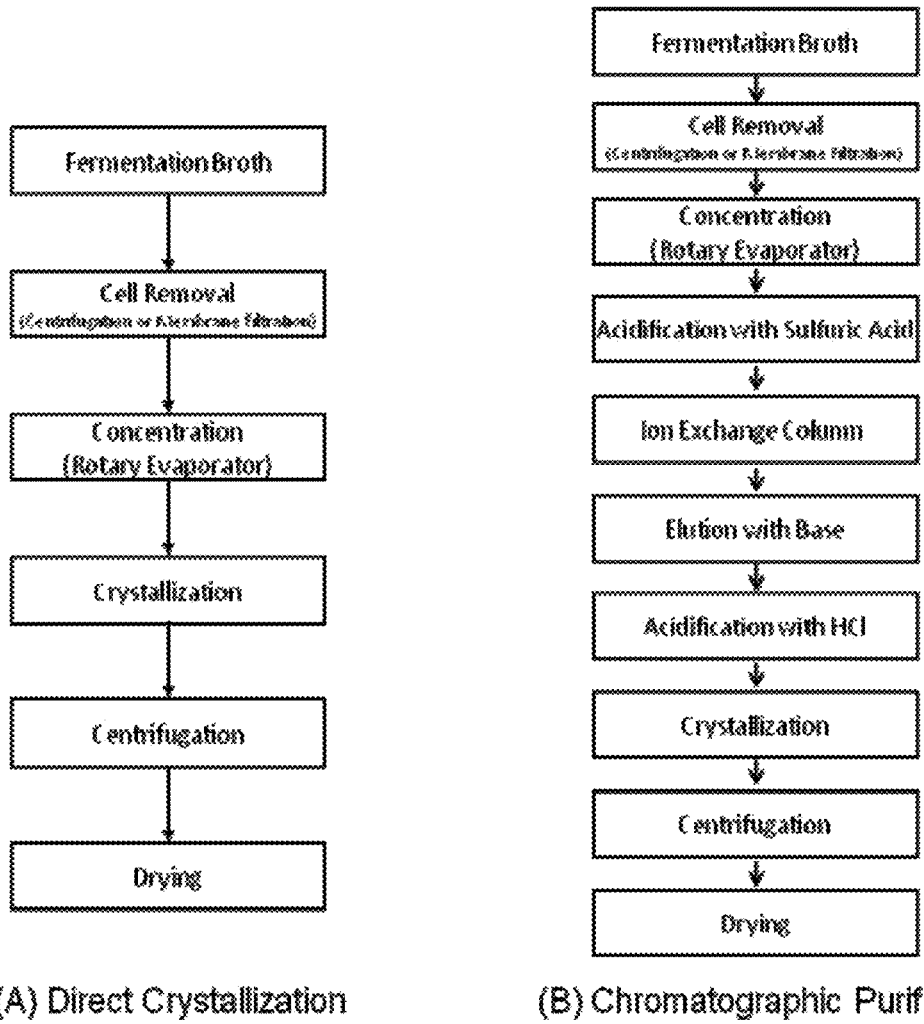

FIG. 15 are schematic flowcharts illustrating embodiments of purification processes for L-Homoalanine from fermentation broth.

DETAILED DESCRIPTION OF THE INVENTION

The techniques and procedures described or referenced herein are generally well understood and commonly employed using conventional methodology by those skilled in the art. As appropriate, procedures involving the use of commercially available kits and reagents are generally carried out in accordance with manufacturer defined protocols and/or parameters unless otherwise noted. Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

As used herein and in the appended claims, the singular forms "a," "an," and "the" include plural referents unless the context clearly dictates otherwise. Thus, for example, reference to "a polynucleotide" includes a plurality of such polynucleotides and reference to "the microorganism" includes reference to one or more microorganisms, and so forth.

Accordingly, metabolically "engineered" or "modified" microorganisms are produced via the introduction of genetic material into a host or parental microorganism of choice thereby modifying or altering the cellular physiology and biochemistry of the microorganism. Through the introduction of genetic material the parental microorganism acquires new properties, e.g. the ability to produce a new, or greater quantities of an intracellular metabolite. In an illustrative embodiment, the introduction of genetic material into a parental microorganism results in a new or modified ability to produce an amino acid such as L-homoalanine. The genetic material introduced into the parental microorganism contains gene(s), or parts of genes, coding for one or more enzymes involved in a biosynthetic pathway for the production of an amino acid (e.g. a modified glutamate dehydrogenase as disclosed herein) and may also include additional elements for the expression and/or regulation of expression of these genes, e.g. promoter sequences.

An engineered or modified microorganism can also include in the alternative or in addition to the introduction of a genetic material into a host or parental microorganism, the disruption, deletion or knocking out of a gene or polynucleotide to alter the cellular physiology and biochemistry of the microorganism. Through the reduction, disruption or knocking out of a gene or polynucleotide the microorganism acquires new or improved properties (e.g., the ability to produced a new or greater quantities of an intracellular metabolite, improve the flux of a metabolite down a desired pathway, and/or reduce the production of undesirable by-products).

Microorganisms provided herein are modified to produce metabolites in quantities not available in the parental microorganism. A "metabolite" refers to any substance produced by metabolism or a substance necessary for or taking part in a particular metabolic process. A metabolite can be an organic compound that is a starting material (e.g., glucose), an intermediate (e.g., 2-ketobutyrate) in, or an end product (e.g., L-homoalanine) of metabolism. Metabolites can be used to construct more complex molecules, or they can be broken down into simpler ones. Intermediate metabolites may be synthesized from other metabolites, perhaps used to make more complex substances, or broken down into simpler compounds, often with the release of chemical energy.

The disclosure identifies specific genes useful in the methods, compositions and organisms of the disclosure; however it will be recognized that absolute identity to such genes is not necessary. For example, changes in a particular gene or polynucleotide comprising a sequence encoding a polypeptide or enzyme can be performed and screened for activity. Typically such changes comprise conservative mutation and silent mutations. Such modified or mutated polynucleotides and polypeptides can be screened for expression of a function enzyme activity using methods known in the art.

A "coding sequence" can be a sequence which "encodes" a particular gene, such as a glutamate dehydrogenase gene, for example. A coding sequence is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A transcription termination sequence will usually be located 3' to the coding sequence.

DNA "control sequences" refer collectively to promoter sequences, ribosome binding sites, polyadenylation signals, transcription termination sequences, upstream regulatory domains, enhancers, and the like, which collectively provide for the transcription and translation of a coding sequence in a host cell. As used herein, the term "promoter" refers to a nucleotide sequence containing elements that initiate the transcription of an operably linked nucleic acid sequence in a desired host microorganism. At a minimum, a promoter contains an RNA polymerase binding site. It can further contain one or more enhancer elements which, by definition, enhance transcription, or one or more regulatory elements that control the on/off status of the promoter. When *E. coli* is used as the host microorganism, representative *E. coli* promoters include, but are not limited to, the β-lactamase and lactose promoter systems (see Chang et al., Nature 275:615-624, 1978), the SP6, T3, T5, and T7 RNA polymerase promoters (Studier et al., Meth. Enzymol. 185:60-89, 1990), the lambda promoter (Elvin et al., Gene 87:123-126, 1990), the trp promoter (Nichols and Yanofsky, Meth. in Enzymology 101:155-164, 1983), and the Tac and Trc promoters (Russell et al., Gene 20:231-243, 1982). When yeast is used as the host microorganism, exemplary yeast promoters include 3-phosphoglycerate kinase promoter, glyceraldehyde-3-phosphate dehydrogenase (GAPDH) promoter, galactokinase (GAL1) promoter, galactoepimerase promoter, and alcohol dehydrogenase (ADH) promoter. Promoters suitable for driving gene expression in other types of microorganisms are also well known in the art.

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof.

Due to the inherent degeneracy of the genetic code, other polynucleotides which encode substantially the same or a functionally equivalent polypeptide can also be used to clone and express the polynucleotides encoding such enzymes. A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences).

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for S. cerevisiae and mammals are UAA and UGA, respectively. The typical stop codon for monocotyledonous plants is UGA, whereas insects and E. coli commonly use UAA as the stop codon (Dalphin et al. (1996) Nucl. Acids Res. 24: 216-218). Methodology for optimizing a nucleotide sequence for expression in a plant is provided, for example, in U.S. Pat. No. 6,015,891, and the references cited therein.

Those of skill in the art will recognize that, due to the degenerate nature of the genetic code, a variety of DNA compounds differing in their nucleotide sequences can be used to encode a given enzyme of the disclosure. The native DNA sequence encoding the biosynthetic enzymes described above are referenced herein merely to illustrate an embodiment of the disclosure, and the disclosure includes DNA compounds of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as they modified or variant polypeptides have the enzymatic anabolic or catabolic activity of the reference polypeptide. Furthermore, the amino acid sequences encoded by the DNA sequences shown herein merely illustrate embodiments of the disclosure.

As used herein, two proteins (or a region of the proteins) are substantially homologous when the amino acid sequences have at least about 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences. Sequence for the genes and polypeptides/enzymes listed herein can be readily identified using databases available on the World-Wide-Web. In addition, the amino acid sequence and nucleic acid sequence can be readily compared for identity using commonly used algorithms in the art.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art.

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

A typical algorithm used comparing a molecule sequence to a database containing a large number of sequences from different organisms is the computer program BLAST (see, e.g. Zhang et al., (1997) Genome Res. 7:649-656; Morgulis et al., (2008) Bioinformatics 15:1757-1764; and Camacho et al., (2008) BMC Bioinformatics 10:421 Ye et al., (2006) Nucleic Acids Res. 34:W6-W9; and Johnson et al., (2008) Nucleic Acids Res. 36:W5-W9), especially blastp or tblastn (see, e.g. Altschul et al., Nucleic Acids Res. 1997 Sep. 1; 25(17): 3389-3402). Typical parameters for BLASTp are:

Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

When searching a database containing sequences from a large number of different organisms, it is typical to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences (see, e.g. Pearson et al., Methods Enzymol. 1990; 183:63-98 hereby incorporated herein by reference). For example, percent sequence identity between amino acid sequences can be determined using FASTA with its default parameters (a word size of 2 and the PAM250 scoring matrix), as provided in GCG Version 6.1, hereby incorporated herein by reference.

It is understood that a range of microorganisms can be modified to include a recombinant metabolic pathway suitable for the production of L-homoalanine. It is also understood that various microorganisms can act as "sources" for genetic material encoding target enzymes suitable for use in a recombinant microorganism provided herein. The term "microorganism" includes prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism. In typical embodiments of the invention, the microorganism is *Escherichia coli* or *Corynebacterium glutamicum*.

A "protein" or "polypeptide", which terms are used interchangeably herein, comprises one or more chains of chemical building blocks called amino acids that are linked together by chemical bonds called peptide bonds. An "enzyme" means any substance, composed wholly or largely of protein, that catalyzes or promotes, more or less specifically, one or more chemical or biochemical reactions. The term "enzyme" can also refer to a catalytic polynucleotide (e.g., RNA or DNA). A "native" or "wild-type" protein, enzyme, polynucleotide, gene, or cell, means a protein, enzyme, polynucleotide, gene, or cell that occurs in nature.

It is understood that the polynucleotides described above include "genes" and that the nucleic acid molecules described above include "vectors" or "plasmids." Accordingly, the term "gene", also called a "structural gene" refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence. The term "nucleic acid" or "recombinant nucleic acid" refers to polynucleotides such as deoxyribonucleic acid (DNA), and, where appropriate, ribonucleic acid (RNA). The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence.

The term "operon" refers two or more genes which are transcribed as a single transcriptional unit from a common promoter. In some embodiments, the genes comprising the operon are contiguous genes. It is understood that transcription of an entire operon can be modified (i.e., increased, decreased, or eliminated) by modifying the common promoter. Alternatively, any gene or combination of genes in an operon can be modified to alter the function or activity of the encoded polypeptide. The modification can result in an increase in the activity of the encoded polypeptide. Further, the modification can impart new activities on the encoded polypeptide. Exemplary new activities include the use of alternative substrates and/or the ability to function in alternative environmental conditions.

A "vector" is any means by which a nucleic acid can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes," that is, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an agrobacterium or a bacterium.

"Expression vector" refers to a nucleic acid that can be introduced into a host cell in order to express a particular polypeptide or polynucleotide in that cell. As is known in the art, an expression vector can be maintained permanently or transiently in a cell, whether as part of the chromosomal or other DNA in the cell or in any cellular compartment, such as a replicating vector in the cytoplasm. An expression vector also comprises a promoter that drives expression of an RNA, which typically is translated into a polypeptide in the cell or cell extract. For example, suitable promoters for inclusion in the expression vectors of the invention include those that function in eukaryotic or prokaryotic host cells. Promoters can comprise regulatory sequences that allow for regulation of expression relative to the growth of the host cell or that cause the expression of a gene to be turned on or off in response to a chemical or physical stimulus. For *E. coli* and certain other bacterial host cells, promoters derived from genes for biosynthetic enzymes, antibiotic-resistance conferring enzymes, and phage proteins can be used and include, for example, the galactose, lactose (lac), maltose, tryptophan (trp), beta-lactamase (b/a), bacteriophage lambda PL, and T5 promoters. In addition, synthetic promoters, such as the tac promoter (U.S. Pat. No. 4,551,433), can also be used. For *E. coli* expression vectors, it is useful to include an *E. coli* origin of replication, such as from pUC, p1P, p1I, and pBR. For efficient translation of RNA into protein, the expression vector also typically contains a ribosome-binding site sequence positioned upstream of the start codon of the coding sequence of the gene to be expressed. Other elements, such as enhancers, secretion signal sequences, transcription termination sequences, and one or more marker genes by which host cells containing the vector can be identified and/or selected, may also be present in an expression vector. Selectable markers, i.e., genes that confer antibiotic resistance or sensitivity, can be used and confer a selectable phenotype on transformed cells when the cells are grown in an appropriate selective medium.

"Transformation" refers to the process by which a vector is introduced into a host cell. Transformation (or transduction, or transfection), can be achieved by any one of a number of means including electroporation, microinjection, biolistics (or particle bombardment-mediated delivery), or agrobacterium mediated transformation.

The disclosure provides nucleic acid molecules in the form of recombinant DNA expression vectors or plasmids, as described in more detail below, that encode one or more target enzymes. Generally, such vectors can either replicate in the cytoplasm of the host microorganism or integrate into the chromosomal DNA of the host microorganism. In either case, the vector can be a stable vector (i.e., the vector remains present over many cell divisions, even if only with selective pressure) or a transient vector (i.e., the vector is gradually lost by host microorganisms with increasing numbers of cell divisions). The disclosure provides DNA molecules in isolated (i.e., not pure, but existing in a preparation in an abundance and/or concentration not found in nature) and purified (i.e., substantially free of contaminating materials or substantially free of materials with which the corresponding DNA would be found in nature) forms.

The various components of an expression vector can vary widely, depending on the intended use of the vector and the host cell(s) in which the vector is intended to replicate or drive expression. Expression vector components suitable for the expression of genes and maintenance of vectors in *Escherichia coli, Corynebacterium glutamicum*, yeast, *Streptomyces*, and other commonly used cells are widely known and commercially available. For example, suitable promoters for inclusion in the expression vectors of the disclosure include those that function in eukaryotic or prokaryotic host microorganisms. Promoters can comprise regulatory sequences that allow for regulation of expression relative to the growth of the host microorganism or that cause the expression of a gene to be turned on or off in response to a chemical or physical stimulus. For *E. coli* and certain other bacterial host cells, promoters derived from genes for biosynthetic enzymes, antibiotic-resistance conferring enzymes, and phage proteins can be used and include, for example, the galactose, lactose (lac), maltose, tryptophan (trp), beta-lactamase (bla), bacteriophage lambda PL, and T5 promoters. In addition, synthetic promoters, such as the tac promoter (U.S. Pat. No. 4,551,433), can also be used. For *E. coli* expression vectors, it is useful to include an *E. coli* origin of replication, such as from pUC, p1P, p1, and pBR.

Thus, typical recombinant expression vectors useful with embodiments of the invention contain at least one expression system, that is, for example, one comprised of at least a functional portion of GDH and/or other biosynthetic gene coding sequences operably linked to a promoter and optionally termination sequences that operate to effect expression of the coding sequence in compatible host cells. The host cells are modified by transformation with the recombinant DNA expression vectors of the disclosure to contain the expression system sequences either as extrachromosomal elements or integrated into the chromosome.

A polynucleotide of the disclosure can be amplified using cDNA, mRNA or alternatively, genomic DNA, as a template and appropriate oligonucleotide primers according to standard PCR amplification techniques and those procedures described in the Examples section below. The nucleic acid so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer.

It is also understood that an isolated nucleic acid molecule encoding a polypeptide homologous to the enzymes described herein can be created by introducing one or more nucleotide substitutions, additions or deletions into the nucleotide sequence encoding the particular polypeptide, such that one or more amino acid substitutions, additions or deletions are introduced into the encoded protein. Mutations can be introduced into the polynucleotide by standard techniques, such as site-directed mutagenesis and PCR-mediated mutagenesis. In contrast to those positions where it may be desirable to make a non-conservative amino acid substitutions (see above), in some positions it is preferable to make conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

As previously discussed, general texts which describe molecular biological techniques useful herein, including the use of vectors, promoters and many other relevant topics, include Berger and Kimmel, Guide to Molecular Cloning Techniques, Methods in Enzymology Volume 152, (Academic Press, Inc., San Diego, Calif.) ("Berger"); Sambrook et al., Molecular Cloning—A Laboratory Manual, 2d ed., Vol. 1-3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel"). Examples of protocols sufficient to direct persons of skill through in vitro amplification methods, including the polymerase chain reaction (PCR), the ligase chain reaction (LCR), Q-replicase amplification and other RNA polymerase mediated techniques (e.g., NASBA), e.g., for the production of the homologous nucleic acids of the disclosure are found in Berger, Sambrook, and Ausubel, as well as in Mullis et al. (1987) U.S. Pat. No. 4,683,202; Innis et al., eds. (1990) PCR Protocols: A Guide to Methods and Applications (Academic Press Inc. San Diego, Calif.) ("Innis"); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Nat'l. Acad. Sci. USA 87: 1874; Lomeli et al. (1989) J. Clin. Chem. 35: 1826; Landegren et al. (1988) Science 241: 1077-1080; Van Brunt (1990) Biotechnology 8: 291-294; Wu and Wallace (1989) Gene 4:560; Barringer et al. (1990) Gene 89:117; and Sooknanan and Malek (1995) Biotechnology 13: 563-564. Improved methods for cloning in vitro amplified nucleic acids are described in Wallace et al., U.S. Pat. No. 5,426,039. Improved methods for amplifying large nucleic acids by PCR are summarized in Cheng et al. (1994) Nature 369: 684-685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the disclosure. Nothing herein is to be construed as an admission that the inventors are not entitled to antedate such disclosure by virtue of prior disclosure.

Typical Embodiments of the Invention

Figure 1B:
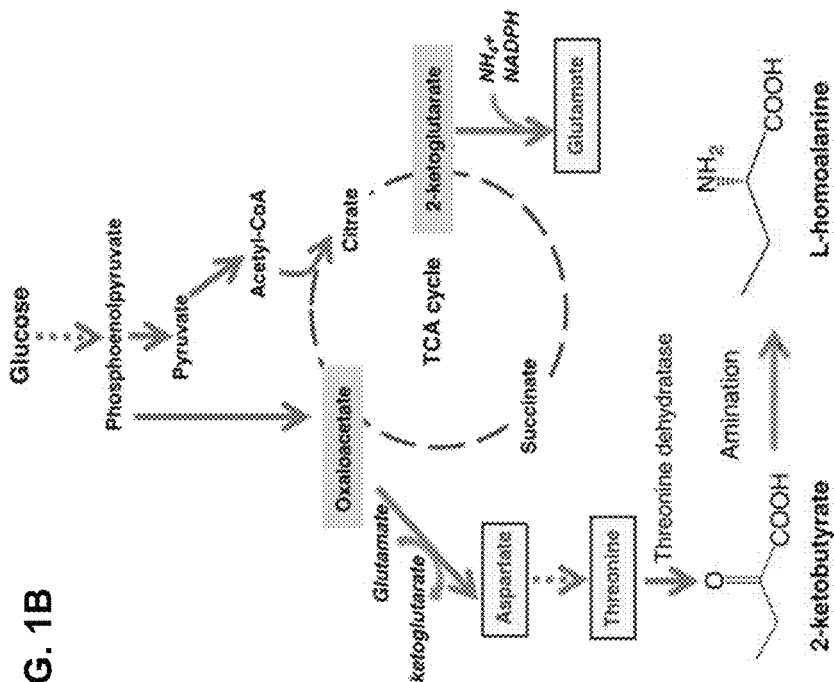
FIG. 1B shows a nonnatural metabolic pathway for L-homoalanine fermentation. Engineered *E. coli* can overproduce the natural amino acid threonine from glucose. Threonine is converted to 2-ketobutyrate by threonine dehydratase. Then L-homoalanine is synthesized from 2-ketobutyrate by amination.
Figure 1A:
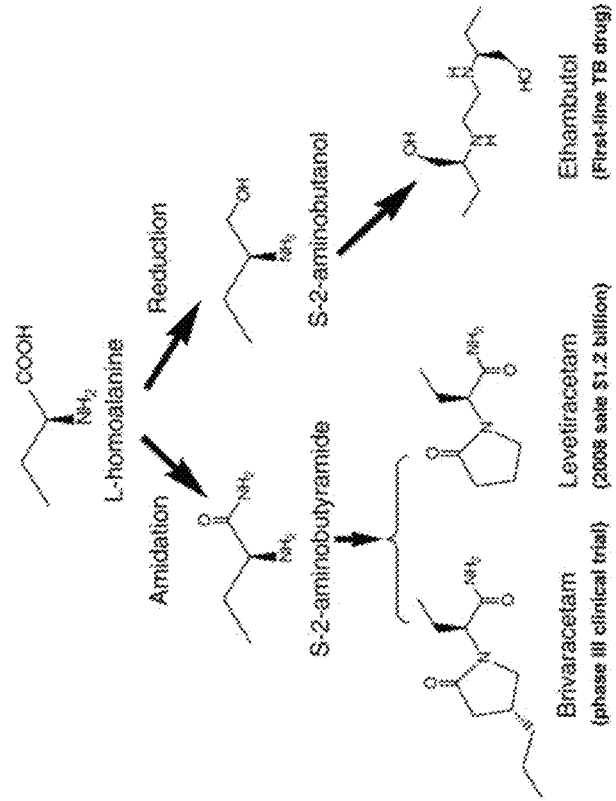
FIG. 1A shows chemical synthetic routes of antiepileptic and antituberculosis drugs from the chiral intermediate L-homoalanine.
Figure 1C:
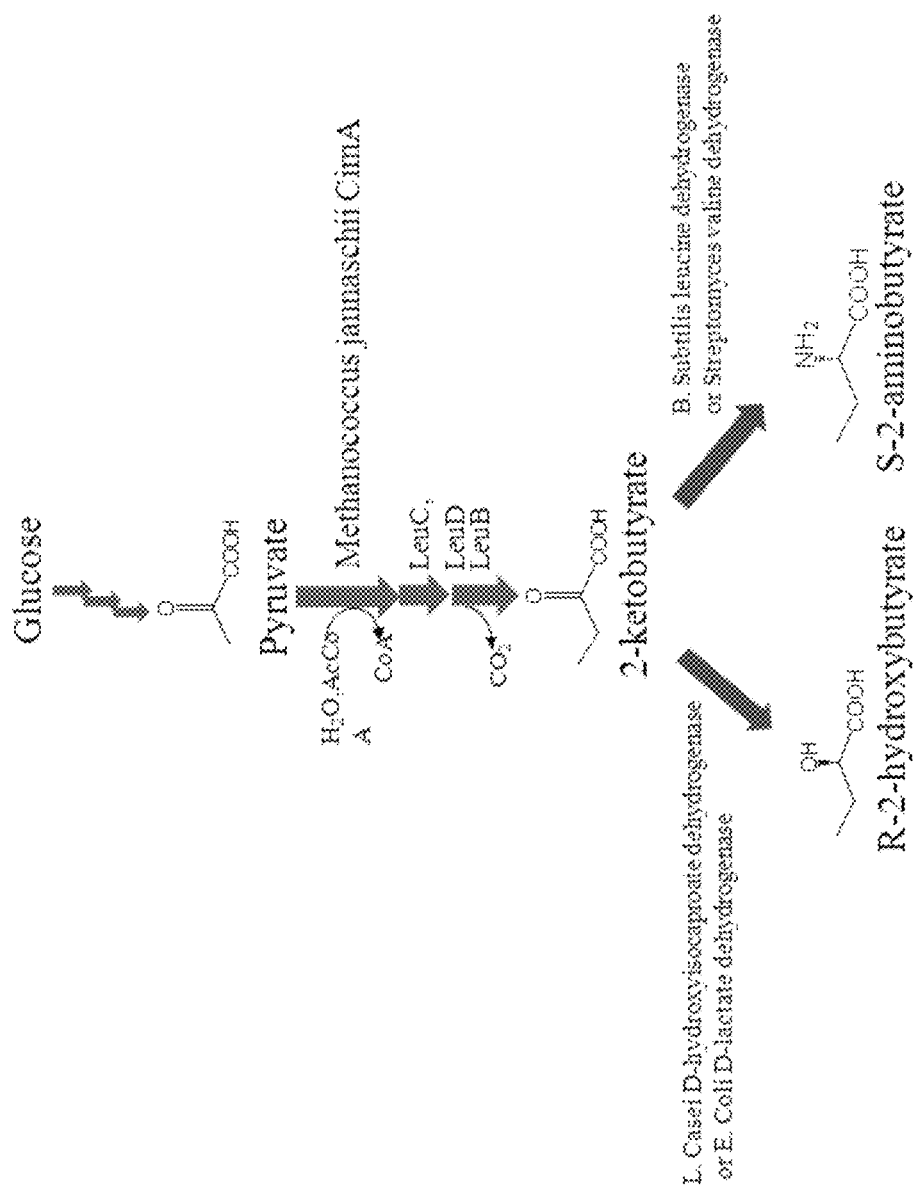
FIG. 1C shows illustrative steps for the biosynthesis of the chiral metabolites R-2-hydroxybutyrate and S-2-aminobutyrate from glucose.
Figure 1D:
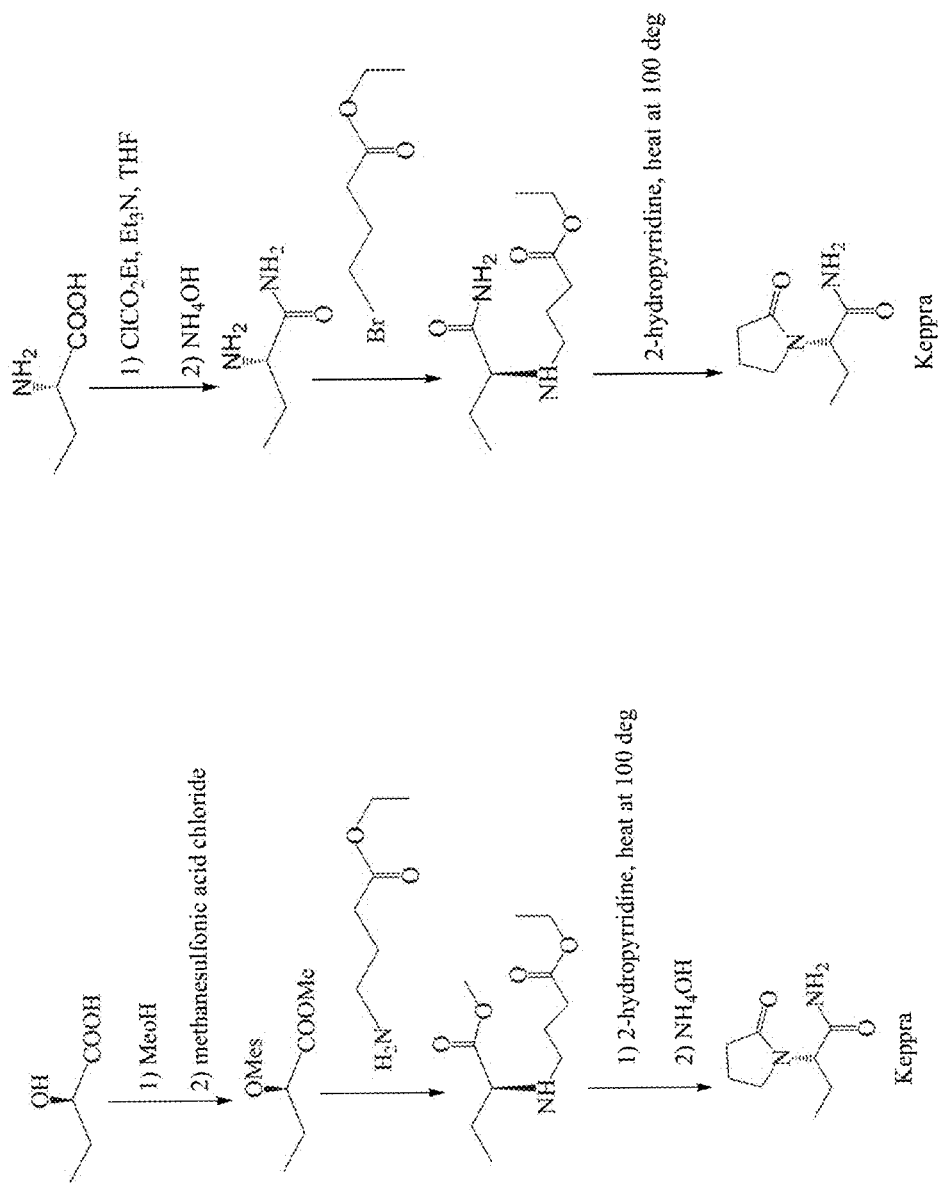
FIG. 1D shows illustrative steps for the enatioselective synthesis of Keppra® from R-2-hydroxybutyrate and S-2-aminobutyrate.

As discussed below, unique metabolic pathways in *Escherichia coli* have been constructed in order to expand the metabolic functions of this organism and, for example, allow its production of L-homoalanine as a metabolite (FIG. 1B). In the wild type metabolic network, glucose is converted to threonine after "glycolysis" and "aspartate biosynthesis" (see, e.g. Debabov V G (2002) Adv Biochem Eng Biot 79:113-136). In this wild type metabolism, threonine can then be converted to 2-ketobutyrate by threonine dehydratase TdcB or IlvA as a precursor for isoleucine biosynthesis. As discussed in detail below, we describe methods and materials that can be used to divert metabolic pathways involving 2-ketobutyrate in order to biosynthesize the nonnatural amino acid L-homoalanine.

In typical embodiments, the metabolically engineered microorganisms disclosed herein comprise one or more biochemical pathways optimized for the production of L-homoalanine. In various aspects, a recombinant microorganism provided herein includes the elevated expression of at least one target enzyme as compared to a parental microorganism. The target enzyme is encoded by, and expressed from, a nucleic acid sequence derived from a suitable biological source. In other embodiments, a recombinant microorganism provided herein includes the decreased expression of at least one target enzyme as compared to a parental microorganism. In some aspects the nucleic acid sequence is a gene derived from a bacterial or yeast source.

A microorganism strain that overly expresses one or more of the enzymes disclosed herein can be obtained as follows. A DNA fragment(s) encoding the one or more of the polypeptides discussed herein can be obtained by polymerase chain reaction from its natural source(s) based on its coding sequence(s), which can be retrieved from GenBank. The DNA fragment(s) is then operably linked to a suitable promoter to produce an expression cassette. In one example, one expression cassette includes one coding sequence operably linked to a promoter. In another example, one expression cassette includes multiple coding sequences, all of which are in operative linkage with a promoter. In that case, it is preferred that a ribosomal binding site is incorporated 5' to each of the coding sequences. If desired, the coding sequences are subjected to codon optimization based on the optimal codon usage in the host microorganism.

The expression cassette(s) described above is then introduced into a suitable microorganism to produce the genetically modified microorganisms disclosed herein. Positive transformants are selected and the over-expression of one or more of the enzymes mentioned above are confirmed by methods known in the art, e.g., immune-blotting or enzymatic activity analysis. The modified microorganisms are then cultured in a suitable medium for L-homoalanine acid production. Preferably, the medium contains glucose for making L-homoalanine. After a sufficient culturing period, the medium is collected and the L-homoalanine is isolated.

The invention disclosed herein has a number of embodiments. One embodiment is a recombinant polypeptide that catalyzes a chemical reaction wherein threonine is converted to 2-oxobutyrate; and typically further catalyzes a chemical reaction wherein this 2-oxobutyrate is then converted to L-homoalanine. Optionally this recombinant polypeptide is encoded in a DNA molecule which can be transformed and expressed in a microbial host (e.g. one encoded by a DNA in an expression vector). Typically the recombinant polypeptide is used in a methodology designed to make an amino acid (e.g. L-homoalanine). A specific illustrative embodiment of the invention is a recombinant microbial host comprising transformed DNA molecules encoding polypeptides that catalyze the conversion of threonine to 2-oxobutyrate; and further the conversion of 2-oxobutyrate to L-homoalanine; so that the microbial host cell produces L-homoalanine.

Another embodiment of the invention is a composition of matter comprising a glutamate dehydrogenase polypeptide having an at least 95% identity to SEQ ID NO: 1, and further comprising as amino acid substitution mutation at residue position K92 and/or T195 (for example K92V and T195S). In certain embodiments of the invention, the glutamate dehydrogenase polypeptide further comprises at least 2-10 substitutions (for example K92L, K92V, T195S, T195A, V377A or S380C), and/or deletion or insertion (e.g. a polyhistidine tag) mutations as compared to the wild type glutamate dehydrogenase polypeptide of SEQ ID NO: 1. Optionally for example, the glutamate dehydrogenase polypeptide includes at least one specific amino acid substitution mutation comprising K92L, K92V, T195S, T195A, V377A or S380C. A related embodiment of the invention is an isolated glutamate dehydrogenase polynucleotide having an at least 95% identity to SEQ ID NO: 2 and encoding a glutamate dehydrogenase polypeptide that comprises at least one mutation at amino acid position K92, T195, V377 or S380; and further exhibits a specificity for 2-ketobutyrate that is greater than its specificity for 2-ketoglutarate (e.g. 2, 4, 8, 10, 20, 30, 40 or 50 fold greater). In the Examples below, the specificity constant $k_{cat}/K_m$ of the GDH2 mutant towards 2-ketobutyrate is shown to be 50-fold higher than that towards the natural substrate 2-ketoglutarate. Compared to transaminase IlvE and NADH-dependent valine dehydrogenases, the evolved glutamate dehydrogenase increased the conversion yield of 2-ketobutyrate to L-homoalanine by over 300% under aerobic conditions.

Embodiments of the invention include compositions comprising the glutamate dehydrogenase polypeptide disclosed herein in combination with an organism such as *Escherichia coli* or *Corynebacterium glutamicum*. In typical embodiments, the *Escherichia coli* or *Corynebacterium glutamicum* organisms have been transformed with an expression vector encoding a glutamate dehydrogenase polypeptide disclosed herein. In certain embodiments of the invention, the organism is a strain of *Escherichia coli* that produces relatively high levels of threonine, for example one that can produce at least 2, 3, 4, 5, 6, 7 or 8 g/L threonine from 30 g/L glucose in a nutrient media.

Certain embodiments of the invention utilize a *Corynebacterium* such as *Corynebacterium glutamicum*. As is known in the art, *Corynebacterium* is a genus of Gram-positive rod-shaped bacteria that are aerobic or facultatively anaerobic, chemoorganotrophs, catalase positive, non-spore-forming, and non-motile (Yassin A F, et al. "*Corynebacterium glaucum* sp. nov." Int. J. Syst. Evol. Microbiol. 53

(Pt 3): 705-9. May 2003). As with *E. coli*, culture conditions for growing Corynebacteria are well known. Corynebacteria strains can require biotin to grow, albeit slowly even on enriched media. Some strains also need thiamine and PABA. (Collins, M. D., et al. "Genus *Corynebacterium* Lehmann and Neumann 1896, 350AL." Bergey's Manual of Systematic Bacteriology, vol. 2, pp. 1266-1276. 1986). The bacteria are known to grow in Loeffler's media, blood agar, and trypticase soy agar (TSA). Non-pathogenic species of *Corynebacterium* are used for industrial applications, such as the production of amino acids, nucleotides, and other nutritional factors. In fact, one of the most studied and biotechnologically important bacterial species is *C. glutamicum*, whose name refers to its capacity to produce glutamic acid in aerobic conditions. (Abe, S., et al. "Taxonomical studies on glutamic acid-producing bacteria." J. Gen. Appl. Microbiol. 13: 279-301. 1976). It is widely known for its role in the production of monosodium glutamate, which is used extensively in the food industry. Today, *C. glutamicum* has been developed for the production of many biogene amino acids, nucleotides, and vitamins and provides an annual production of more than two million tons of amino acids, mainly L-glutamate and L-lysine. (Burkovski, Andreas. "Corynebacteria: Genomics and Molecular Biology." Caister Academic Press, June 2008).

Culture conditions (e.g. nutrient medias) suitable for the growth and maintenance of recombinant microorganisms are well known in the art (see, e.g. Handbook of Microbiological Media, Fourth Edition (2010), Ronald M. Atlas (Author); and Fermentation Microbiology and Biotechnology, Third Edition (2006) E. M. T. El-Mans (Editor), C. F. A. Bryce (Editor), Arnold L. Demain (Editor) and A. R. Allman (Editor)). The skilled artisan will recognize that such conditions can be modified to accommodate the requirements of each microorganism. Appropriate culture conditions useful in producing L-homoalanine comprise conditions of culture medium pH, ionic strength, nutritive content, etc.; temperature; oxygen/$CO_2$/nitrogen content; humidity; and other culture conditions that permit production of the compound by the host microorganism, i.e., by the metabolic action of the microorganism. Appropriate culture conditions are well known for microorganisms that can serve as host cells.

In some embodiments of the invention the organism is selected to have a mutation in one or more genes in a metabolic pathway in order to facilitate L-homoalanine production, for example a strain of *Escherichia coli* that comprises a mutation in a rhtA polypeptide of SEQ ID NO: 5, one resulting in a decreased threonine export activity as compared to wild type SEQ ID NO: 5. In some embodiments of the invention the organism is selected to overexpress one or more polypeptides in addition to the glutamate dehydrogenase polypeptides disclosed herein, for example, one comprising an expression vector encoding a threonine dehydratase polypeptide having an at least 95% identity to SEQ ID NO: 6 or SEQ ID NO: 7. Optionally, the organism can synthesize L-homoalanine at a concentration of at least 0.5, 1.0, 1.5, 2.0, 2.5, 3.0, 3.5, 4.0, 4.5, or 5.0 g/L in a nutrient media.

The instant disclosure allows artisans to generate a variety of recombinant polypeptides, for example a substantially purified GDH polypeptide comprising SEQ ID NO:1 having at least mutations at one or more of the following positions: K92, T195, V377 or S380, and a specificity for 2-ketobutyrate that is greater than its specificity for 2-ketoglutarate. The instant disclosure also provides a substantially purified GDH polypeptide having from 1-30, 1-20, 1-10 or 1-5 conservative amino acid substitutions and a specificity for 2-ketobutyrate that is greater than its specificity for 2-ketoglutarate. The instant disclosure similarly provides a substantially purified polypeptide comprising a sequence that is at least 70%, 80%, 85%, 90%, 95%, 98% or 99% identical to SEQ ID NO: 1 and wherein the polypeptide comprises a substituted amino acid residue position selected from the group consisting of a K92, T195, V377 or S380 as well as a specificity for 2-ketobutyrate that is greater than its specificity for 2-ketoglutarate.

Embodiments of the invention include methods for making L-homoalanine. One such embodiment of the invention is a method for making L-homoalanine comprising: placing an *Escherichia coli* or *Corynebacterium glutamicum* organism into a nutrient medium, wherein the organism comprises a glutamate dehydrogenase polypeptide having an at least 90-95% identity to SEQ ID NO: 1 and an amino acid substitution mutation at residue position K92 or T195. This organism is then cultured in a nutrient medium under conditions that allows it to biosynthesize L-homoalanine. Typically the glutamate dehydrogenase polypeptide used in such methods further comprises at least 2-10 substitution, deletion or insertion mutations as compared to the wild type glutamate dehydrogenase polypeptide of SEQ ID NO: 1. In certain embodiments of the invention, the organism is *Escherichia coli* comprising a mutation in a polypeptide having an at least 90-95% identity to a rhtA polypeptide of SEQ ID NO: 5 and is one that results in a decreased threonine export activity as compared to wild type rhtA. Optionally the organism is transformed with an expression vector encoding a threonine dehydratase polypeptide having an at least 95% identity to SEQ ID NO: 6 or SEQ ID NO: 7.

In illustrative embodiments of the invention, the organism is grown under at least one of the following conditions: at a temperature between 30-40° C.; for a time period between at least 4 to at least 48 hours; at a pH between 6-8; and/or in a nutrient media comprising M9, LB, F1 or TB media. In one illustrative embodiment, the nutrient medium comprises M9 medium; and the organism is a strain of *Escherichia coli* selected for its ability to make at least 2, 3, 4, 5, 6, 7 or 8 g/L threonine from 30 g/L glucose in the M9 medium. Typically in these methods, the organism can make L-homoalanine at a concentration of at least 0.5, 1.0, 1.5, 2.0, 2.5, 3.0, 3.5, 4.0, 4.5 or 5.0 g/L in a nutrient media.

Yet another embodiment of the invention is a method for aminating 2-ketobutyrate so as to form L-homoalanine, the method comprising combining 2-ketobutyrate with a glutamate dehydrogenase polypeptide having an at least 95% identity to SEQ ID NO: 1, wherein: the glutamate dehydrogenase polypeptide comprises at least two amino acid substitution mutations at residue positions K92, T195, V777 or S380; and the glutamate dehydrogenase polypeptide has a specificity for 2-ketobutyrate that is greater than its specificity for 2-ketoglutarate. In these methods, the 2-ketobutyrate is combined with the glutamate dehydrogenase polypeptide under conditions which allow L-homoalanine to be formed.

Certain embodiments of the methods for making L-homoalanine include further steps to purify L-homoalanine. In describing compounds such as L-homoalanine, those of skill in the art understand that this language is intended to encompass these compounds as well as the salts of these compounds (e.g. pharmaceutically acceptable salts known in the art). For example, as is known in the art, L-homoalanine can occur both a free acid form as well as a L-homoalanine sodium, potassium or ammonium salts, and other salts derived from alkaline earth elements or other metallic salts.

Some embodiments of the invention include at least one purification step comprising lysis of cells of an isolated organism used to make L-homoalanine (e.g. those in a L-homoalanine fermentation broth). Embodiments can include at least one purification step comprising centrifugation of cells or cell lysates of an isolated organism used to make L-homoalanine. Embodiments can include at least one purification step comprising precipitation of one or more compounds present in a medium used to make L-homoalanine (e.g. L-homoalanine itself). Embodiments can include at least one purification step comprising the filtration and/or the concentration of one or more compounds present in a nutrient media (e.g. L-homoalanine). Embodiments can include at least one purification step comprising a chromatographic separation of one or more compounds present in a nutrient media (e.g. L-homoalanine).

Certain embodiments of the methods disclosed herein include further chemical or biochemical synthesis steps using a L-homoalanine composition made according to an embodiment of the invention. In illustrative methods, L-homoalanine is chemically modified by, for example, performing an chemical reaction such as an amidation or a reduction reaction on this compound in order to generate further compounds such as S-2-aminobutyramide, S-2-aminobutanol, levetiracetam, brivaracetam or ethambutol (see, e.g. FIG. 1). In specific embodiments of the invention, L-homoalanine is chemically manipulated in a process designed to make amino acid amides. Illustrative chemical synthesis processes that can be adapted for use with embodiments of the invention are known and the art and disclosed, for example, in U.S. Pat. Nos. 4,696,943 and 7,531,673, the contents of which are incorporated herein by reference. In illustrative embodiments of the invention, the process can include reacting an amino acid, or acid salt of an amino acid, with a halogenating agent, or with a substance that reacts with carboxylic acids to form a leaving group, to form an intermediate, then reacting the intermediate with ammonia. When the amino acid or acid salt is enantiomerically pure, the amide will be a stereoisomer. Amides made by such processes can be used, for example, to form levetiracetam.

Embodiments of the invention also include articles of manufacture and/or kits designed to facilitate the methods of the invention. Typically such kits include instructions for using the elements therein according to the methods of the present invention. Such kits can comprise a carrier means being compartmentalized to receive in close confinement one or more container means such as vials, tubes, and the like, each of the container means comprising one of the separate elements to be used in the method. One of the containers can comprise a vial, for example, containing an expression vector encoding a polypeptide disclosed herein, for example one encoding a glutamate dehydrogenase polypeptide having an altered substrate specificity. Optionally the expression vector has been transformed into an organism such as *Escherichia coli* or *Corynebacterium glutamicum* in order to facilitate their production of L-homoalanine. One such embodiment of the invention is a kit for synthesizing L-homoalanine, the kit comprising: an expression vector encoding a glutamate dehydrogenase polypeptide having an at least 95% identity to SEQ ID NO: 1 and an amino acid substitution mutation at residue position K92 or T195; as well as a container for this expression vector. Optionally the kit further comprises an expression vector encoding a threonine dehydratase polypeptide having an at least 95% identity to SEQ ID NO: 6 or SEQ ID NO: 7 and/or a live *Escherichia coli* strain (e.g. a strain of *Escherichia coli* that overexpresses threonine and/or one that comprises a mutation in a rhtA polypeptide of SEQ ID NO: 5 resulting in a decreased threonine export activity as compared to wild type SEQ ID NO: 5).

In a typical embodiment of the invention, an article of manufacture containing materials useful for production of L-homoalanine is provided. The article of manufacture comprises a container and a label. Suitable containers include, for example, bottles, vials, syringes, and test tubes. The containers may be formed from a variety of materials such as glass or plastic. The container can hold a composition of matter which can be used to produce L-homoalanine (e.g. an organism transformed with an expression vector encoding a recombinant GDH polypeptide). The label on, or associated with, the container indicates that the composition is used for making L-homoalanine. The article of manufacture may further comprise a second container comprising another composition or substrate in addition to a GDH polynucleotide. This composition or substrate, for example, might be used to increase the production of certain intermediaries in the production of L-homoalanine, such as threonine. It may further include other materials desirable from a commercial and user standpoint, including other buffers, diluents, filters, needles, syringes, and package inserts with instructions for use. Further biological aspects of the invention are discussed in the following Examples.

EXAMPLES

The Examples below provide illustrative methods and materials that can be used in the practice the various embodiments of the invention disclosed herein.

Example 1

Illustrative Methods and Materials for Biosynthesizing L-Homoalanine Directly from Glucose Expanding Metabolic Network for Biosynthesis of L-Homoalanine.

There are two major challenges in this expanded biosynthetic pathway: the first challenge we face is to find the right amination enzyme to convert 2-ketobutyrate into L-homoalanine and existing enzymes may not work since L-homoalanine cannot be detected in normal cells (see, e.g. Epelbaum S, et al. (1998) J Bacteriol 180(16):4056-4067) even though 2-ketobutyrate is a natural metabolite; the second is evolving metabolism to drive the carbon flux towards 2-ketobutyrate. In most organisms, 2-ketobutyrate is synthesized via threonine. Alternative routes include "the pyruvate pathway" starting with the condensation of acetyl-CoA and pyruvate to form citramalate (see, e.g. Charon et al. (1974) J Bacteriol 117(1):203-211), "the glutamate pathway" via $\beta$-methylaspartate and $\beta$-methyloxaloacetate (see, e.g. Phillips et al. (1972) J Bacteriol 109(2):714-719), or "$\gamma$ elimination" of activated substrates such as O-phospho-homoserine and O-acetyl-homoserine (see, e.g. Donini S, et al. (2006) Biochem Biophys Res Commun 350(4):922-928). We choose "the threonine pathway" because there are existing technologies in the fermentation industry to develop bacteria strains that could produce more than 100 WL threonine (see, e.g. Debabov V G (2002) Adv Biochem Eng Biot 79:113-136).

Limitation of Natural Enzymes on Amination of 2-Ketobutyrate.

Figure 2:
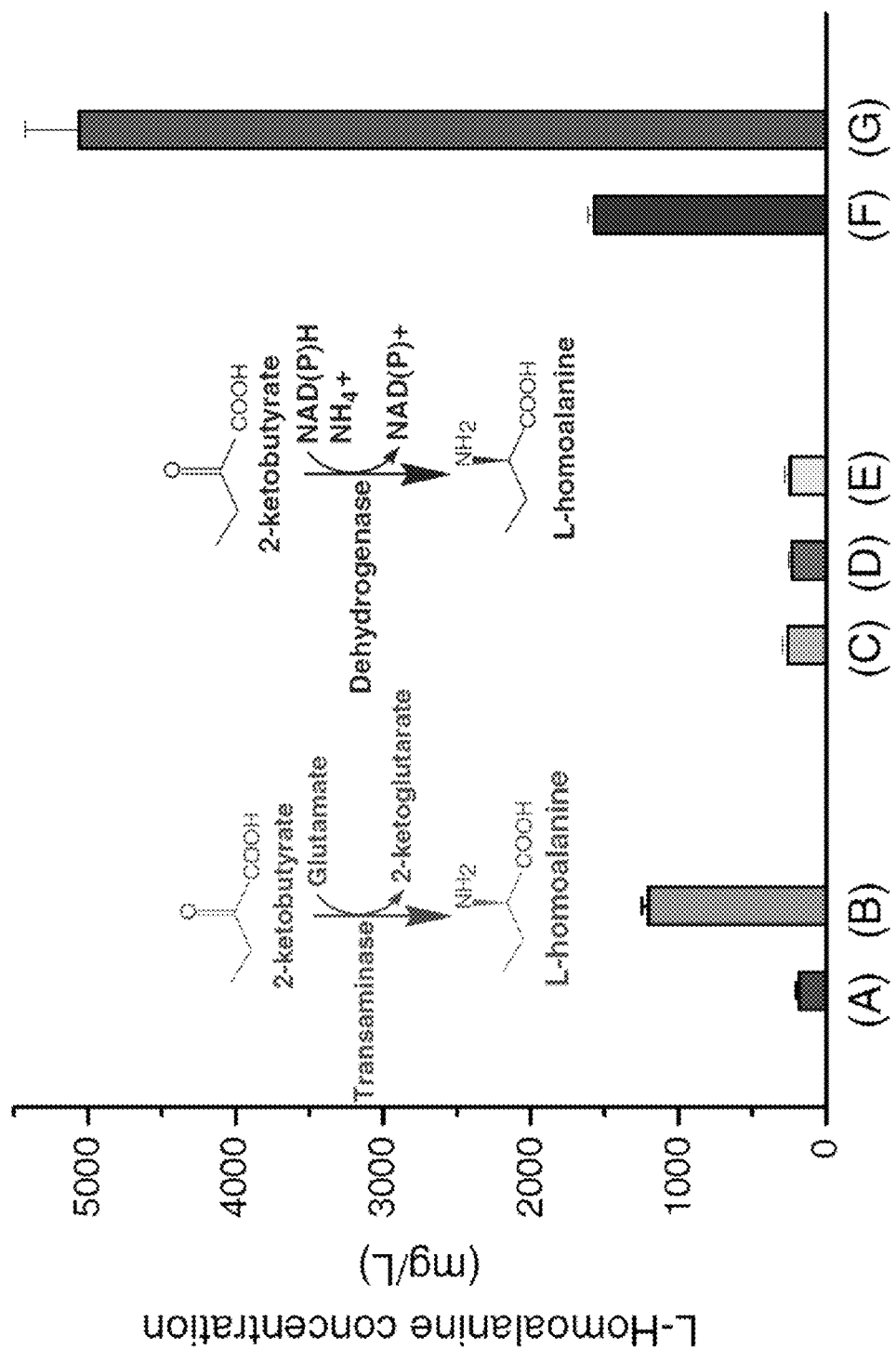
FIG. 2 is a graph comparing different amination enzymes on the production of L-homoalanine. *E. coli* cultures were inoculated in M9 medium with addition of 10 g/L 2-ketobutyrate and incubated at 37° C. for 24 h. The horizontal axis labels are defined as follows: (A) Wild-type *E. coli* BW25113; overexpression of (B) transaminase IlvE (C) valine dehydrogenase from *Streptomyces avermitilis*; (D) valine dehydrogenase from *Streptomyces coelicolor*, (E) valine dehydrogenase from *Streptomyces fradiae*; (F) evolved glutamate dehydrogenase GDH1; and (G) evolved glutamate dehydrogenase GDH2. The error bars represent standard deviations from three independent experiments.

In order to check if any endogenous transaminase of *E. coli* can work on 2-ketobutyrate, we fed 10 g/L 2-ketobutyrate to wildtype *E. coli* strain BW25113 growing in M9 medium. After 24 h, HPLC analysis showed that only 182 mg/L L-homoalanine was produced (FIG. 2A). Since the branched-chain amino acid aminotransferase IlvE (see, e.g. Inoue K, et al. (1988) J Biochem 104(5):777-784) is likely to be a functional candidate, we cloned and overexpressed IlvE in BW25113, which increased the production of L-homoalanine to 1.2 WL (FIG. 2B). Additional feeding of 10 g/L amino donor glutamate further increased the L-homoalanine titer to 3.2 g/L. These experiments demonstrated that transaminases such as IlvE could aminate 2-ketobutyrate into L-homoalanine. However, high concentration of glutamate is needed to drive the reaction equilibrium because transamination is a reversible reaction process. Even under such extreme conditions, the conversion rate of transaminating 2-ketobutyrate to L-homoalanine is only 32%.

Direct reductive amination of ketoacids with ammonia is a preferable choice to produce amino acid because it avoids the usage of glutamate as the amino donor (see, e.g. Zhang et al. (2007) Appl Microbiol Biotechnol 77(2):355-366). Compared to transamination, reductive amination could potentially simplify the metabolic manipulation and reduce the production cost. It has been shown previously that valine dehydrogenases from various *Streptomyces* species are active on reductive amination of 2-ketobutyrate in vitro (see, e.g. Priestley et al. (1989) Biochem J 261(3):853-861; Turnbull et al. (1997) J Biol Chem 272(40):25105-25111). We thus cloned and overexpressed in BW25113 the valine dehydrogenases from *Streptomyces avermitilis, Streptomyces coelicolor,* and *Streptomyces fradiae*. Unfortunately, these dehydrogenases only slightly increased the L-homoalanine titer (around 240~260 mg/L, FIG. 2C-E) as compared to the BW25113 background (182 mg/L). The possible reason is that valine dehydrogenase is a catabolic enzyme that favors the reaction direction towards degradation of L-homoalanine instead of biosynthesis in aerobic condition.

Evolving Glutamate Dehydrogenase to Aminate 2-Ketobutyrate.

Figure 3C:
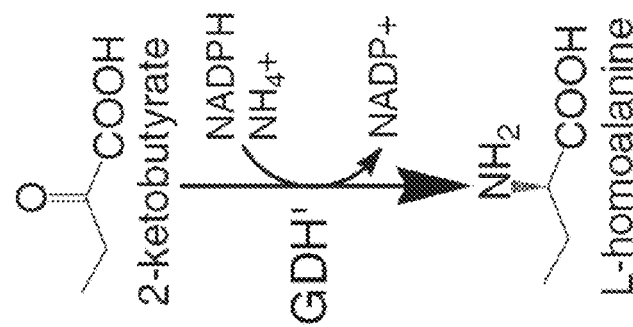
FIG. 3C shows that 2-ketobutyrate is chemically similar to the valine precursor, 2-ketoisovalerate. A mutant GDH active on 2-ketoisovalerate is likely to be active on 2-ketobutyrate.
Figure 3B:
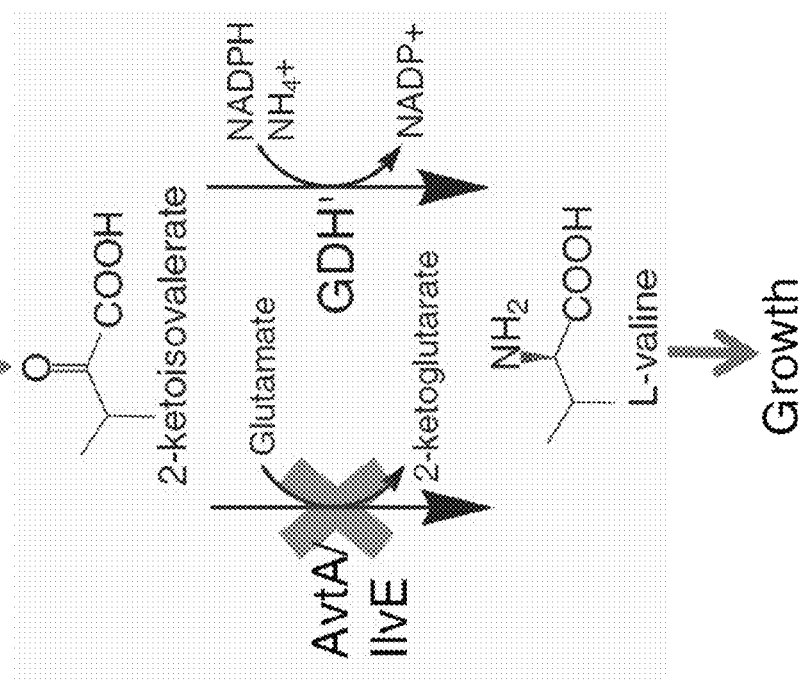
FIG. 3B shows that knocking out transaminase genes avtA and ilvE from the chromosome makes wild-type *E. coli* valine auxotrophic, which can be complemented by a mutant GDH active on aminating 2-ketoisovalerate.
Figure 3A:
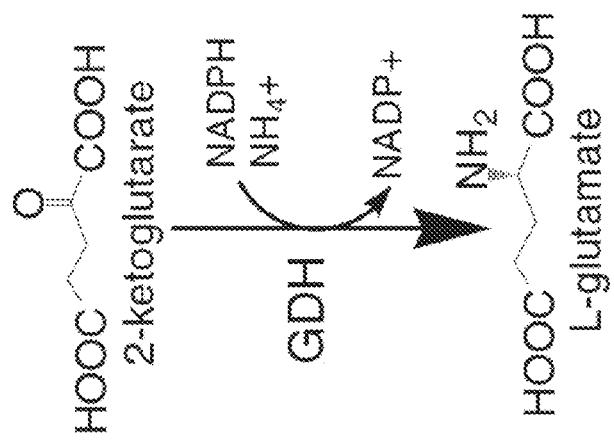
FIG. 3A shows that wild-type GDH assimilates ammonia directly into glutamate.
Figure 8:
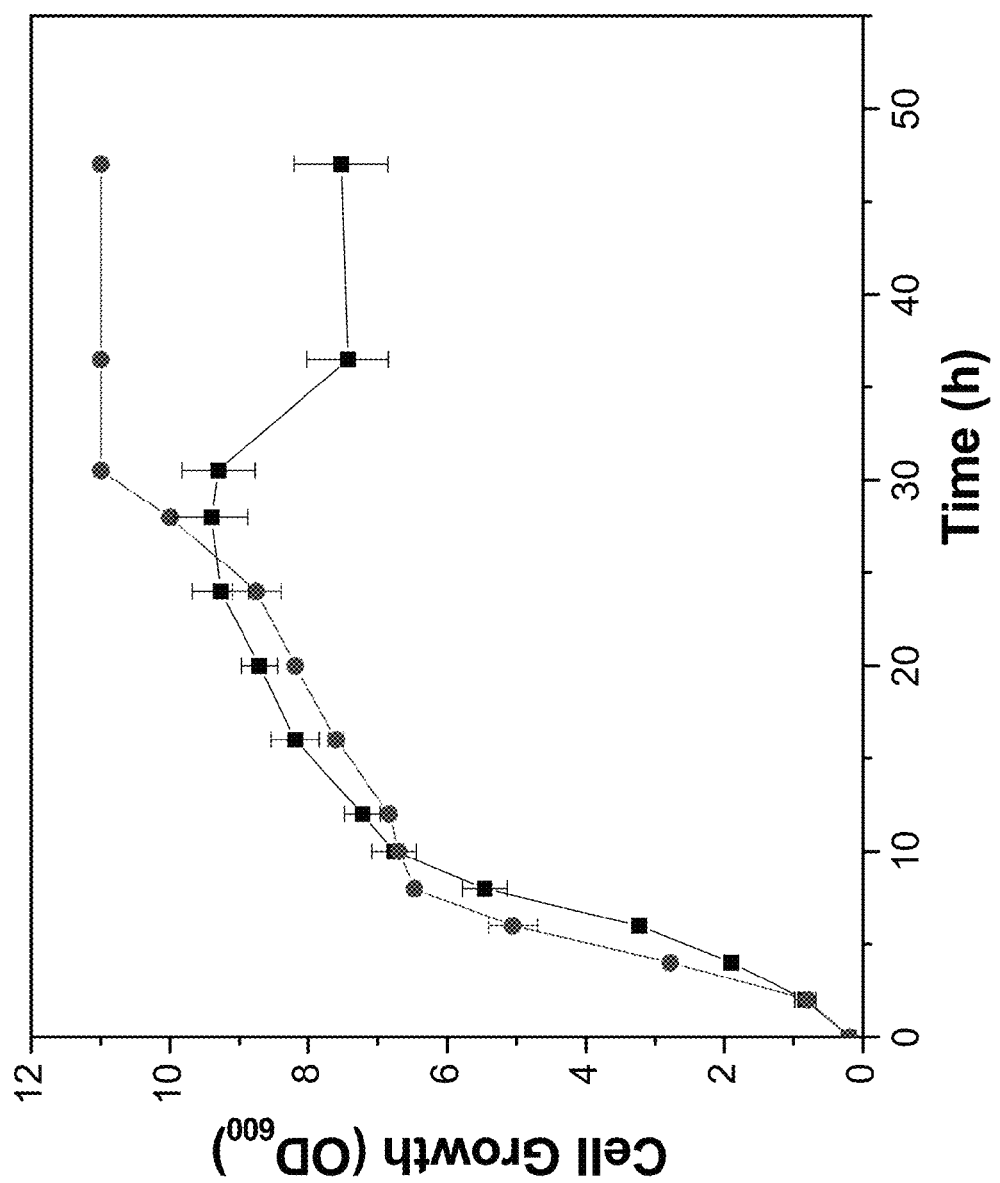
FIG. 8 is a graph illustrating the time courses for the growth of *E. coli* strains at OD$_{600}$ (optical density at 600 nm). Cells were incubated in production medium at 33° C. Circles represent wild type strain ATCC98082 with pZS_thrO; diamonds represent best production strain ATCC98082 (ΔrhtA) with pZS_thrO and pZElac_ilvA$_{BS}$ GDH. The error bars represent standard deviations from three independent experiments.
Figure 9:
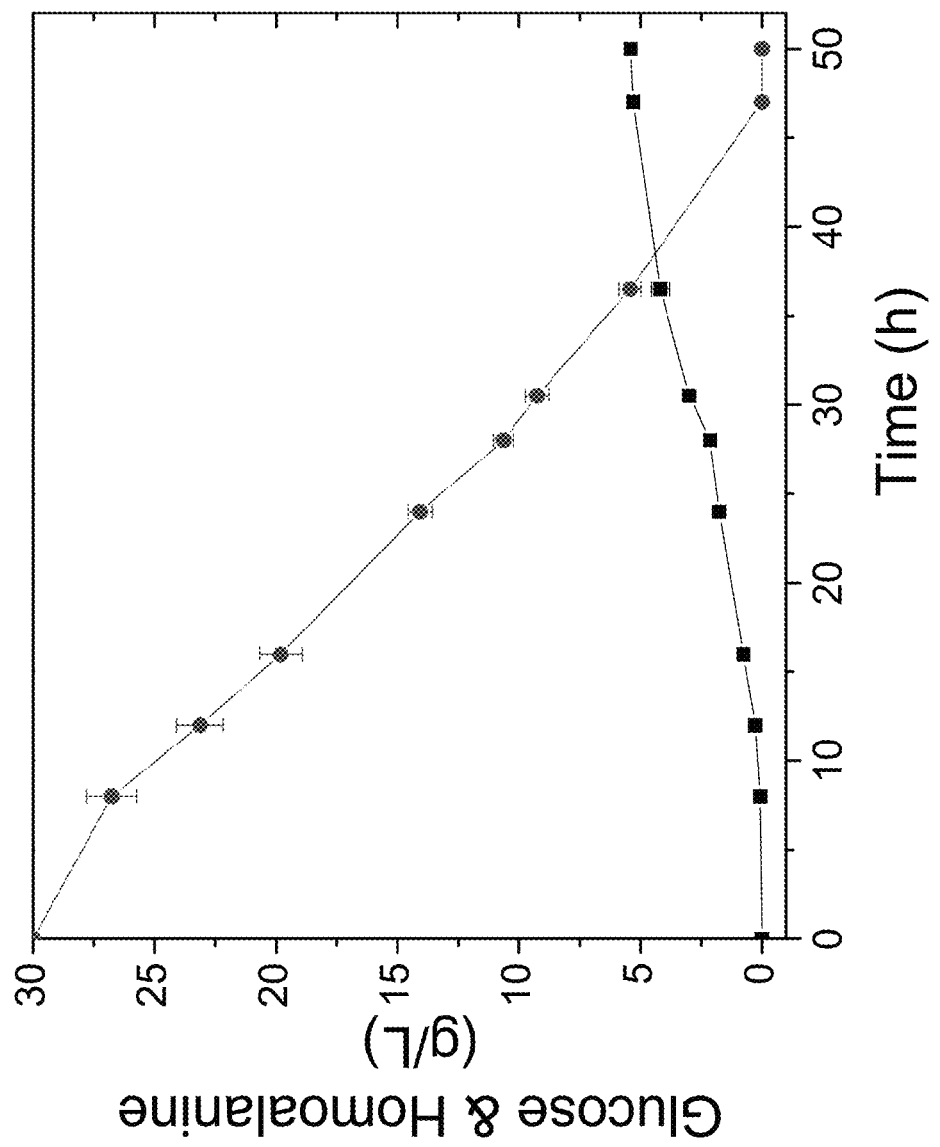
FIG. 9 is a graph illustrating the time courses for the production of L-homoalanine. Diamonds represent L-homoalanine concentration; circles represent residual glucose concentration. The error bars represent standard deviations from three independent experiments.

Glutamate is formed by reductive amination of 2-ketoglutarate with ammonia. The reaction is catalyzed by glutamate dehydrogenase (GDH) or glutamate synthase in the presence of cofactor NADPH (FIG. 3A). This ammonia utilization process is very efficient since glutamate is the universal nitrogen source of other amino acids. The catalytic activity of GDH towards biosynthesis of glutamate is more than 10 times higher than that towards degradation of glutamate (see, e.g. Sharkey et al. (2009) Proteins 77(2): 266-278), which makes GDH an ideal biosynthetic enzyme for amino acid production. However, since native GDH is active only on 2-ketoglutarate, we need to engineer GDH to obtain new substrate specificity towards 2-ketobutyrate for L-homoalanine biosynthesis.

To this end, we have developed a selection strategy to evolve GDH. Deletion of transaminase genes avtA and ilvE from the chromosome makes wild-type *E. coli* valine auxotrophic (see, e.g. Wang et al. (1987) J Bacteriol 169(9):4228-4234), whose growth in minimal medium can be rescued by a mutant GDH active on aminating the valine precursor 2-ketoisovalerate (FIG. 3B). Since the chemical structures of 2-ketobutyrate and 2-ketoisovalerate are similar, we reasoned that GDH variants active on 2-ketoisovalerate could be active on 2-ketobutyrate (FIG. 3C).

Based on the crystal structure of *Clostridium symbiosum* glutamate dehydrogenase (PDB: 1BGV) (see, e.g. Stillman et al. (1993) J Mol Biol 234(4):1131-1139), residues K89, T193, V377, and S380 are within a radius of 6 Å of the γ-carbon of glutamate substrate (FIG. 4A). Sequence alignment of GDH between *C. symbiosum* and *E. coli* shows that the binding pocket is conserved, and the corresponding residues of *E. coli* GDH are K92, T195, V377, and S380 (FIG. 4B). These sites were subjected to site-saturation mutagenesis by PCR gene assembly using primers containing degenerate NNK (N ¼ A, T, G, C; K ¼ G, T) codons. The assembled fragments were ligated into plasmid pZE12 (see, e.g. Lutz et al. (1997) Nucleic Acids Res 25(6):1203-1210) and the resulting library was transformed into the valine auxotrophic *E. coli* (ΔavtA, ΔilvE). The library contained 2 million independent clones and the selection was performed in M9 minimal medium. Two mutants were isolated: GDH1 has K92L, T195A, V377A, and S380C mutations; GDH2 has K92V and T195S mutations.

Characterization of the Evolved Glutamate Dehydrogenase Mutants.

As can be seen in FIG. 4C, while *E. coli* (ΔavtA, ΔilvE) without plasmid could not grow in the absence of valine in minimal medium, GDH mutants could support cell growth without valine addition. In particular, the growth speed of GDH2 transformant in minimal medium was very close to that in valine-supplemented medium, which means that GDH2 successfully rescued the valine auxotrophic phenotype. The evolved GDH mutants were transformed and overexpressed in BW25113. Feeding of 10 WL 2-ketobutyrate into such transformants produced 1.6 WL (GDH1) and 5.1 WL (GDH2) L-homoalanine (FIG. 2F, G). Interestingly, the production yield is in agreement with the growth speed of these two GDH mutants in minimal medium. These results suggest that our selection strategy works well and the selected GDH2 is more active on both 2-ketoisovalerate and 2-ketobutyrate than GDH1. GDH2 transformant has a conversion yield of 50% and a productivity of 5.1 g/L/day, much better than the IlvE transformant plus high concentration of glutamate.

To characterize the enzymes, both the wild-type glutamate dehydrogenase GDHwt and mutant GDH2 were added an N-terminal 6×His-tag, overexpressed, and purified through Ni-NTA columns. The kinetic parameters for activation of 2-ketoglutarate (cognate substrate) and 2-ketoisovalerate or 2-ketobutyrate (nonnatural substrates) were determined by monitoring the consumption of NADPH at 340 nm (FIG. 6). The enzymatic assay indicates that towards 2-ketoglutarate the specificity constant $k_{cat}/K_m$ of GDH2 is nearly 3,000-fold smaller than that of GDHwt. While the two enzymes have a similar $K_m$ towards 2-ketoisovalerate, GDH2 has a five times higher $k_{cat}$ than GDHwt and can produce valine for cell growth in physiological condition. Compared to GDHwt, GDH2 has a significant enhanced catalytic activity on 2-ketobutyrate with a 4-fold decrease in $K_m$ (8.4 mM vs. 35.4 mM) and a 2-fold increase in kat (90.2 s-1 vs. 47.2 s-1). The increase in binding affinity is very helpful since high concentration of 2-ketobutyrate interferes with cellular metabolic activities (see, e.g. Daniel et al. (1983) Mol Gen Genet 190(3):452-458). On the basis of the crystallographic model for the active site of GDH, amino group of K92 hydrogenbonds to the γ-carboxyl group of 2-ketoglutarate and determines the substrate specificity (see, e.g. Stillman et al. (1993) J Mol Biol 234(4):1131-1139). Mutation of lysine to valine increases the hydrophobic character of the binding pocket, which explains why the specificity constant $k_{cat}/K_m$ of GDH2 towards 2-ketobutyrate is 50-fold higher than that towards the natural substrate 2-ketoglutarate.

Optimizing the Full Biosynthetic Pathway of L-Homoalanine.

Through directed evolution, we obtained a mutant glutamate dehydrogenase GDH2 that is highly active on amination of 2-ketobutyrate. When we overexpressed GDH2 in BW25113, 0.1 g/L L-homoalanine was produced from 30 WL glucose (column #2 in FIG. 5A). Without overexpression of GDH2, no homoalanine was detected (column #1 in FIG. 5A). Now the remaining challenge is to engineer metabolism to divert the carbon flux towards 2-ketobutyrate. Since 2-ketobutyrate is derived from threonine, we switched the production host from wild-type E. coli BW25113 to a threonine overproducer ATCC98082 (see, e.g. Debabov V G (2002) Adv Biochem Eng Biot 79:113-136). E. coli strain ATCC98082 can produce 8 g/L threonine from 30 g/L glucose. Overexpression of GDH2 and threonine dehydratase TdcB in ATCC98082 resulted in production of 0.18 g/L L-homoalanine (column #3 in FIG. 5A) and 3.7 g/L threonine. The high concentration of remaining threonine means that the catabolic enzyme TdcB is not active enough to fully convert threonine into 2-ketobutyrate. Another consequence is the accumulation of 4 g/L glutamate because low concentration of 2-ketobutyrate cannot compete with 2-ketoglutarate for amination by GDH2. We then cloned the biosynthetic threonine dehydratases IlvA from E. coli (IlvAEC) and Bacillus subtilis (see, e.g. Shulman A, et al. (2008) Biochemistry 47(45):11783-11792) (IlvABS). In combination with GDH2, these dehydratases significantly increased the production of L-homoalanine (column #4 and 5 in FIG. 5A). IlvABS was the best enzyme identified and its transformant produced 3.8 g/L L-homoalanine. However, there was still 2.5 g/L threonine remained in the fermentation medium. It is known that ATCC98082 has an rhtA23 mutation which enhances about 10-fold the expression of the rhtA gene (see, e.g. Debabov V G (2002) Adv Biochem Eng Biot 79:113-136), whose protein product is a strong threonine exporter. We reasoned that the active efflux of threonine might account for the extracellular accumulation of threonine. After deletion of rhtA from the ATCC98082 chromosome, threonine no longer accumulated and the concentration of L-homoalanine increased to 5.4 g/L (column #6 in FIG. 5A). This final strain has a productivity of 2.7 g/L/day and a yield of 0.18 g/g glucose (FIG. 5B), which is 26% of the theoretical maximum (the calculation detail is described later herein). Interestingly, even though GDH used significant amounts of cellular reducing power, improving NADPH availability by phosphoglucose isomerase (pgi) knockout (see, e.g. Chemler et al. (2009) Metab Eng 10.1016/j.ymben.2009.07.003) decreased the L-homoalanine production titer to 3.0 g/L, which indicated that threonine biosynthesis was affected by the intracellular redox status.

This work expanded the E. coli metabolism to biosynthesize a nonnatural amino acid L-homoalanine directly from glucose. The success here demonstrates that metabolic manipulation not only allows the production of natural metabolites, but also enables the microbial synthesis of nonnatural metabolites. While traditional metabolic engineering deals with flux engineering, to achieve industry-level biosynthesis of unique chemicals, three steps (pathway expansion, protein evolution, and flux enhancing) should be taken. Protein evolution is a key step since unique enzymes need to be developed to perform nonnatural activities. Here we have evolved the glutamate dehydrogenase to fix ammonia directly onto 2-ketobutyrate, which avoids the usage of glutamate as nitrogen donor and significantly improves the yield of L-homoalanine.

Developing a fermentation process for L-homoalanine (5.4 g/L titer and 0.18 g/g glucose yield in shake flasks) provides a renewable supply of this chiral chemical and enables the synthesis of levetiracetam without expensive chiral chromatography. The greener manufacturing process of levetiracetam could potentially reduce the drug cost (see, e.g. U.S. Pat. No. 4,696,943; U.S. Pat. No. 6,107,492), which may help 50 million epilepsy patients worldwide considering 90% of these people are in developing countries and do not receive the appropriate treatment (see, e.g. Scott et al. (2001) B World Health Organ 79:344-351).

Example 2

Illustrative Materials and Methods Useful to Make and Use Embodiments of the Invention Vector Construction.

All cloning procedures were carried out in the E. coli strain XL10-gold (Stratagene). PCR reactions were performed with KOD polymerase (Novagen). Oligos were synthesized by Operon Biotechnologies (sequence details described later herein). A gene fragment encoding lac repressor Lad (see, e.g. Zhang et al. (2008) Proc Natl. Acad Sci USA 105(52):20653-20658) was inserted into the SacI site of plasmid pZE12 (see, e.g. Lutz et al. (1997) Nucleic Acids Res 25(6):1203-1210) to yield plasmid pZElac. The ilvE gene was amplified from the genomic DNA of E. coli K12 using the primers IlvEaccfwd and IlvExbarev. The valine dehydrogenase genes were amplified from the genomic DNA of Streptomyces avermitilis, Streptomyces coelicolor, and Streptomyces fradiae using the primer pairs VDHsaaccfwd/VDHsaxbarev, VDHscaccfwd/VDHscxbarev, and VDHsfaccfwd/VDHsfxbarev. The glutamate dehydrogenase gene gdhA was amplified from the genomic DNA of E. coli K12 using the primers GDHecaccfwd and GDHecxbarev. All the PCR products were digested with Acc65I and XbaI and ligated into pZElac to yield plasmids pZElac_IlvE, pZElac_VDHsa, pZElac_VDHsc, pZElac_VDHsf and pZElac_GDH. The E. coli threonine dehydratase genes tdcB and ilvA were amplified from the genomic DNA of E. coli K12 using the primer pairs TdcBaccfwd/TdcBsalrev and IlvAecaccfwd/IlvAecsalrev. The Bacillus threonine dehydratase gene ilvA were amplified from the genomic DNA of Bacillus subtilis using the primer pair IlvAbsaccfwd/IlvAbssalrev. These fragments were digested with Acc65I and San. Then they were ligated with mutant GDH gene fragment digested with San and XbaI (amplified with primer pair GDHecsalfwd/GDHecxabrev). The ligated fragments were inserted into pZElac to create plasmids pZElac_tdcB_GDH, pZElac_ilvAEC_GDH and pZElac_ilvABS_GDH.

Knocking out Chromosomal Genes.

Gene deletion was performed using P1 transduction and the strains used for the P1 transduction were obtained from the Keio collection (see, e.g. Baba T, et al. (2006) Mol Syst Biol 2:1-11 (2006.0008)). Colonies containing the correct deletions were transformed with plasmid pCP20 to remove the kanamycin resistance marker. Valine transaminase genes avtA and ilvE were deleted from the E. coli strain BW25113 chromosome to make a valine auxotroph designated as ValK. The threonine exporter gene rhtA was inactivated from the chromosome of threonine-hyperproduction E. coli strain ATCC98082 to improve the production of L-homoalanine.

Construction and Selection of GDH Library.

Oligonucleotides encoding degenerate NNK (N is A, T, G, C; K is G, T) codons at the sites corresponding to Lys-92, Thr-195, Val377, and Ser380 in *E. coli* GdhA were used for library construction. Four separate PCRs were performed by using pZElac_GDH as the template and the following pairs of primers: GDHecaccfwd and GDH_k92lib_rev, GDH_k92lib and GDH_T195lib_rev, GDH_T195lib and GDH_VSlib_rev, GDH_VSlib and GDHecxabrev. The DNA fragments obtained from these PCRs were electrophoresed and purified by using Zymo-spin columns (Zymo Research). Equimolar quantities of the fragments were mixed and subjected to 10 rounds of PCR. The primers GDHecaccfwd and GDHecxabrev were subsequently added, and the reaction mixture was subjected to 25 more rounds of PCR. The resulting 1.4-kb PCR product was digested Acc65I and XbaI and ligated into PZElac digested with the same enzymes. The ligation mixture was transformed into electrocompetent ElectroMAX DH10B cells (Invitrogen), yielding 2 million independent transformants. The plasmid DNA from the pooled transformants was isolated and used to transform into valine auxotroph ValK through electroporation, yielding 10 million independent clones.

Pooled transformants (500 µL, ~109 cells) were incubated in 30 mL of M9 medium containing 20 g/L glucose and 50 mg/L ampicillin with shaking at 37° C. for 2 d. 50 µL of culture was subcultured into two new culture tubes (100× dilution). After another five rounds of successive subculturing the enrichment (to ensure the best mutant dominated in the culture), two mutants were isolated: GDH1 has K92L, T195A, V377A and S380C mutations; and GDH2 has K92V and T195S mutations.

Protein Purification and Enzymatic Assay.

Both gene fragments encoding wildtype glutamate dehydrogenase and GDH2 were amplified using primers GDHbamfwd and GDHbamrev. After digestion with BamHI, the gene fragments were inserted into expression plasmid pQE9 (Qiagen). The resulting expression plasmids were transformed into *E. coli* strain BL21(DE3) harboring pREP4 (Qiagen). Cells were inoculated from an overnight preculture at 1/100 dilution and grown in 200 mL 2XYT rich medium containing 50 mg/L ampicillin and 25 mg/L kanamycin. At an $OD_{600}$ of 0.6, recombinant proteins were expressed by induction of the cell cultures with 0.1 mM IPTG, followed by incubation at 30° C. overnight. Overexpressed proteins were then purified with Ni-nitrilotriacetic acid columns. Protein concentration was determined by measuring UV absorbance at 280 nm.

Enzymatic assay was performed in assay buffer (100 mM Tris buffer, pH 8.0) containing 0.2M NH4Cl, 0.2 mM NADPH, and various concentrations of 2-ketoacids. The reactions were started by adding the purified enzymes, and the consumption of NADPH was monitored at 340 nm (extinction coefficient, 6.22 $mM^{-1}$ $cm^{-1}$). Kinetic parameters ($k_{cat}$ and $K_m$) were determined by fitting initial velocity data to the Michaelis-Menten equation using Origin.

Production of L-Homoalanine.

To test the conversion of 2-ketobutyrate to L-homoalanine, plasmids pZElac_IlvE, pZElac_VDHsa, pZElac_VDHsc, pZElac_VDHsf, pZElac_GDH and pZElac_GDH2 were transformed into BW25113. The transformants were inoculated in M9 medium with 5 g/L yeast extract, 10 g/L ammonium hydrochloride and 20 g/L glucose. Once OD reached ~1.0, 10 g/L 2-ketobutyrate plus 0.1 mM IPTG were added and incubated at 37° C. for 24 h. Amino acids were quantified as o-phthaldialdehyde (OPA) derivatives by HPLC analysis.

To test the production of L-homoalanine from glucose, *E. coli* strain ATCC98082 harboring plasmid pZS_thrO (see, e.g. Zhang et al. (2008) Proc Natl Acad Sci USA 105(52): 20653-20658) was transformed with pZElac_tdcB_GDH, pZElac_ilvAEC_GDH and pZElac_ilvABS_GDH. These transformants were subjected to fermentation using the following production medium: 30 g glucose, 17 g $(NH_4)_2SO_4$, 2 g $KH_2PO_4$, 1 g $MgSO_4 \cdot 7H_2O$, 2 g yeast extract, 0.1 g L-valine, 0.01 g $FeSO_4 \cdot 7H_2O$ and 0.01 g $MnSO_4 \cdot 7H_2O$ per liter. Antibiotics were added appropriately (ampicillin 50 mg/L, spectinomycin 25 mg/L). Overnight 2XYT culture were diluted 25× into fermentation medium and 0.1 mM isopropyl-b-D-thiogalactoside (IPTG) was added to induce protein expression. In shake flask experiments, the culture medium was buffered by addition of 30 g/L $CaCO_3$. Cultures were incubated in 33° C. shaker (250 rpm) for 40-50 h until glucose was consumed.

Theoretical Yield Calculations.

To calculate the theoretical yield of homoalanine from glucose, linear programming optimization using MATLAB software was used. We first establish a set of mass balance equations describing all the relevant intracellular metabolites in terms of input and output fluxes. The input glucose flux is set to 1, so that the yield of isobutanol is equal to the isobutanol flux ($v_{iBOH}$) divided by 1. To calculate the maximal theoretical yield, we carry out the following minimization:

$$\min(-v_{iBOH}) \text{ such that } AV=B$$

Figure 10:
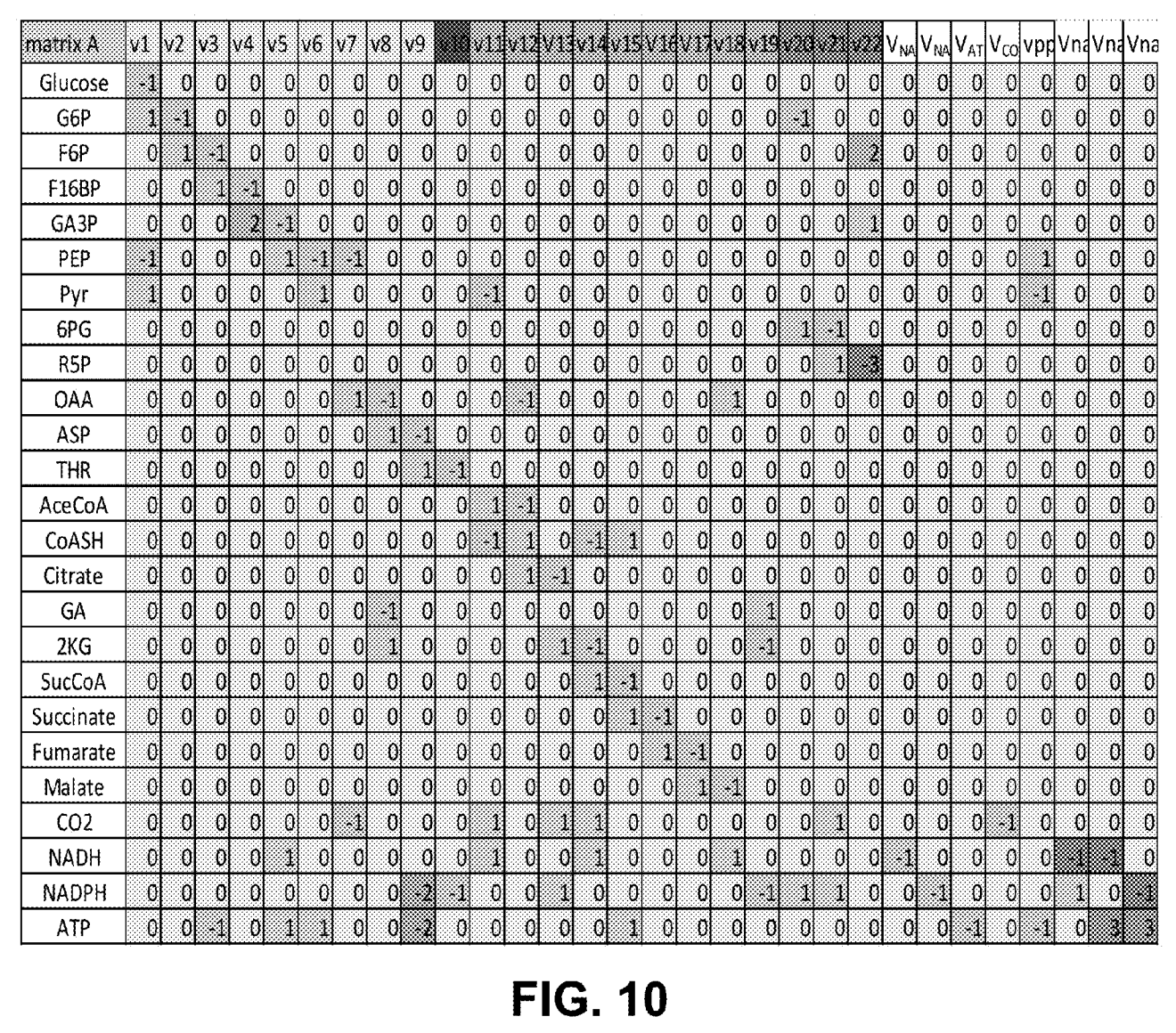

Here A is the stoichiometric matrix (FIG. 10), V is the vector of flux in each reaction included, and B is the vector consists of negative glucose input and zeros (FIG. 11). The rows of A and B correspond to each metabolite, and the columns of A correspond to each reaction (or lumped reaction) considered (defined in FIG. 12).

To carry out this linear optimization problem, we used a MATLAB module "linprog", which uses the following formalism $$\min_x f^T x$$

such that $A_{eq}x=b_{eq}$

To fit this formalism the f vector is defined in FIG. 12

After minimization, V10 is the maximum theoretical yield of isobutanol and the rest of the V (or x) vector is the flux distribution over the metabolic network.

In this calculation, there are two degrees of freedom: 1) whether NADH can be converted to NADPH by transhydrogenase, and 2) the P/O ratio (number of ATP obtained by oxidizing NAD(P)H). FIG. 13 shows the results of the maximum theoretical yield for various combination of these two variations. It is assumed that: 1) energy production from UQH2 derived from succinate dehydrogenase in TCA cycle was not included; and 2) non-oxidative branch of Pentose Phosphate Pathway was assumed 3R5P→2F6P+GA3P.

Example 3

Illustrative Methods for Making and Purifying L-Homoalanine

L-Homoalanine Fermentation.

The expression vector, pZElac_ilvABS_GDH2, was transformed into *E. coli* ATCC98082 with rhtA knock-out. The resulting strain was used for the production test in 5 L fermentor. For the L-homoalanine production experiment in 5 L fermentor, a loop of fresh transformant cells were inoculated into 100 ml LB (in 500 ml flask) containing 100

μg/L Ampicillin. This seed culture was incubated at 34° C., 250 rpm in Innova4000 incubator (New Brunswick Scientific, Edison, N.J.). After overnight growth, this seed culture was used as inoculums for the main fermentation. Fermentor (Bioflo 310, New Brunswick Scientific, Edison, N.J.) was prepared with the production medium contained (per liter): glucose (40 g), $(NH_4)_2SO_4$ (15 g), $KH_2PO_4$ (2 g), $MgSO_47H_2O$ (1 g), Yeast Extract (2 g), L-Valine (0.1 g), $FeSO_47H_2O$ (0.01 g), and $MnSO_47H_2O$ (0.01 g). The pH was adjusted and controlled to 6.8 with 7% $NH_4OH$. The fermentor was controlled at 34° C., 700 rpm and 1 vvm aeration with air. IPTG was added initially to have a final concentration of 0.1 mM. Ampicillin (100 μg/L) was also added to make sure plasmid stability. Feed medium containing 76 g of glucose and 1 g of $KH_2PO_4$ in 200 ml was prepared for feeding after initial glucose (40 g/L) was consumed. After all 80 g/L of glucose consumed, fermentation was stopped.

FIG. 14 shows the result of fermentation using 5 L fermentor. The final titer of L-homoalanine in fermentation broth was 12.2 g/L from 80 g/L glucose consumption. Production yield was 15.25%.

L-Homoalanine Purification.

For the efficient purification of L-homoalanine from fermentation broth, we designed two different purification processes, direct crystallization and chromatographic purification, as shown in FIG. 15. To test the purification process for L-homoalanine, fermentation broth, which had 12 g/L of final L-homoalanine, was used. E. coli cells were removed by either centrifugation (4000 rpm, 10 min) or membrane filtration. This was used as mother liquid for the purification process. For direct crystallization process, the mother liquid (400 ml) was first concentrated to have at least 100 g/L concentration using rotary evaporator (50° C., 100 rpm). The resulting volume, 20 ml (20 fold concentrate), was heated to 70° C. For the crystallization, 50 ml of cool methanol (20° C.) was added to this concentrated broth continuously using pump with 5 ml/min flow rate. White crystal was collected by centrifugation (4000 rpm, 10 min). Crystal can be washed with cool methanol. Purified crystal was dried in oven at 80° C. for 5 hours. In this way, we could purify more than 80% (81%, 3.88 g/4.80 g) of L-homoalanine from fermentation broth.

For the chromatographic purification, concentrated mother liquid prepared as described above was acidified with 5N $H_2SO_4$ to have pH lower than 2.0. Chromatographic column was prepared in 20 cm long glass column (ID 2 cm) packed with Amberlite strongly acidic cation exchanger sodium form resin (Sigma). Before applying concentrated mother liquid into column, the cation-exchange column (50 ml bed volume) was pre-equilibrated with 2-3 bed volumes of acidic water (pH<4). The acidified mother liquid was applied to pre-equilibrated column. To elute L-homoalanine, 3N $NH_4OH$ was applied to the column. Every bed volume (50 ml) was collected to analyze best scheme for collection. Elutes collected at 2nd~3rd bed volume was found to have more than 95% of L-homoalanine applied. The collected liquid was re-acidified with 5N HCl to have pH lower than 2.0. If the concentration at this stage is lower than 100 g/L, more concentration is needed for the optimum crystallization efficiency. The rest of crystallization, washing (if needed) and drying steps are same as described above. In this chromatographic purification process, we could purify more than 70% (73%, 3.50 g/4.80 g) of L-homoalanine from fermentation broth.

Tables:

TABLE 1

Glutamate Dehydrogenase (GDH) polypeptide

```
LOCUS: AAA87979 447 aa linear BCT 10 Feb. 2004
DEFINITION: glutamate dehydrogenase
[Escherichia coli].
ACCESSION: AAA87979 CAA25495
VERSION: AAA87979.1 GI:146124
DBSOURCE: locus ECOGDHA accession J01615.1
SOURCE: Escherichia coli
ORGANISM: Escherichia coli
MDQTYSLESFLNHVQKRDPNQTEFAQAVREVMTTLWPFLEQNPKYRQM

SLLERLVEPERVIQFRVVWVDDRNQIQVNRAWRVQFSSAIGPYKGGMR

FHPSVNLSILKFLGFEQTFKNALTTLPMGGGKGGSDFDPKGKSEGEVM

RFCQALMTELYRHLGADTDVPAGDIGVGGREVGFMAGMMKKLSNNTAC

VFTGKGLSFGGSLIRPEATGYGLVYFTEAMLKRHGMGFEGMRVSVSGS

GNVAQYAIEKAMEFGARVITASDSSGTVVDESGFTKEKLARLIEIKAS

RDGRVADYAKEFGLVYLEGQQPWSLPVDIALPCATQNELDVDAAHQLI

ANGVKAVAEGANMPTTIEATELFQQAGVLFAPGKAANAGGVATSGLEM

AQNAARLGWKAEKVDARLHHIMLDIHHACVEHGGEGEQTNYVQGANIA

GFVKVADAMLAQGVI (SEQ ID NO: 1)
```

TABLE 2

Glutamate Dehydrogenase (GDH) polynucleotide

```
LOCUS ECOGDHA 1779 bp DNA linear BCT 10 Feb. 2004
DEFINITION Escherichia coli glutamate
dehydrogenase (gdhA) gene, complete cds.
ACCESSION J01615 K00565 M23171 X00988
VERSION J01615.1 GI:146123
SOURCE Escherichia coli
CCGGGTGGCAAAACTTTAGCGTCTGAGGTTATCGCATTTGGTTATGAGAT

TACTCTCGTTATTAATTTGCTTTCCTGGGTCATTTTTTTCTTGCTTACCG

TCACATTCTTGATGGTATAGTCGAAAACTGCAAAAGCACATGACATAAAC

AACATAAGCACAATCGTATTAATATATAAGGGTTTTATATCTATGGATCA

GACATATTCTCTGGAGTCATTCCTCAACCATGTCCAAAAGCGCGACCCGA

ATCAAACCGAGTTCGCGCAAGCCGTTCGTGAAGTAATGACCACACTCTGG

CCTTTTCTTGAACAAAATCCAAAATATCGCCAGATGTCATTACTGGAGCG

TCTGGTTGAACCGGAGCGCGTGATCCAGTTTCGCGTGGTATGGGTTGATG

ATCGCAACCAGATACAGGTCAACCGTGCATGGCGTGTGCAGTTCAGCTCT

GCCATCGGCCCGTACAAAGGCGGTATGCGCTTCCATCCGTCAGTTAACCT

TTCCATTCTCAAATTCCTCGGCTTTGAACAAACCTTCAAAAATGCCCTGA

CTACTCTGCCGATGGGCGGTGGTAAAGGCGGCAGCGATTTCGATCCGAAA

GGAAAAAGCGAAGGTGAAGTGATGCGTTTTTGCCAGGCGCTGATGACTGA

ACTGTATCGCCACCTGGGCGCGGATACCGACGTTCCGGCAGGTGATATCG

GGGTTGGTGGTCGTGAAGTCGGCTTTATGGCGGGATGATGAAAAAGCTC

TCCAACAATACCGCCTGCGTCTTCACCGGTAAGGGCCTTTCATTTGGCGG

CAGTCTTATTCGCCCGGAAGCTACCGGCTACGGTCTGGTTTATTTCACAG

AAGCAATGCTAAAACGCCACGGTATGGGTTTTGAAGGGATGCGCGTTTCC
```

TABLE 2 -continued

Glutamate Dehydrogenase (GDH) polynucleotide

GTTTCTGGCTCCGGCAACGTCGCCCAGTACGCTATCGAAAAAGCGATGGA

ATTTGGTGCTCGTGTGATCACTGCGTCAGACTCCAGCGGCACTGTAGTTG

ATGAAAGCGGATTCACGAAAGAGAAACTGGCACGTCTTATCGAAATCAAA

GCCAGCCGCGATGGTCGAGTGGCAGATTACGCCAAAGAATTTGGTCTGGT

CTATCTCGAAGGCCAACAGCCGTGGTCTCTACCGGTTGATATCGCCCTGC

CTTGCGCCACCCAGAATGAACTGGATGTTGACGCCGCGCATCAGCTTATC

GCTAATGGCGTTAAAGCCGTCGCCGAAGGGGCAAATATGCCGACCACCAT

CGAAGCGACTGAACTGTTCCAGCAGGCAGGCGTACTATTTGCACCGGGTA

AAGCGGCTAATGCTGGTGGCGTCGCTCATCGGGCCTGGAAATGGCACAA

AACGCTGCGCCTGGGCTGGAAAGCCGAGAAAGTTGACGCACGTTTGCA

TCACATCATGCTGGATATCCACCATGCCTGTGTTGAGCATGGTGGTGAAG

GTGAGCAAACCAACTACGTGCAGGGCGCGAACATTGCCGGTTTTGTGAAG

GTTGCCGATGCGATGCTGGCGCAGGGTGTGATTTAAGTTGTAAATGCCTG

ATGGCGCTACGCTTATCAGGCCTACAAATGGGCACAATTCATTGCAGTTA

CGCTCTAATGTAGGCCGGGCAAGCGCAGCGCCCCGGCAAAATTTCAGGC

GTTTATGAGTATTTAACGGATGATGCTCCCCACGGAACATTTCTTATGGG

CCAACGGCATTTCTTACTGTAGTGCTCCCAAAACTGCTTGTCGTAACGAT

AACACGCTTCAAGTTCAGCATCCGTTAAC (SEQ ID NO: 2)

TABLE 3

Mutant Glutamate Dehydrogenase-1 (GDH1)

MDQTYSLESFLNHVQKRDPNQTEFAQAVREVMTTLWPFLEQNPKYRQM

SLLERLVEPERVIQFRVVWVDDRNQIQVNRAWRVQFSSAIGPYLGGMR

FHPSVNLSILKFLGFEQTFKNALTTLPMGGGKGGSDFDPKGKSEGEVM

RFCQALMTELYRHLGADTDVPAGDIGVGGREVGFMAGMMKKLSNNTAC

VFAGKGLSFGGSLIRPEATGYGLVYFTEAMLKRHGMFEGMRVSVSGS

GNVAQYAIEKAMEFGARVITASDSSGTVVDESGFTKEKLARLIEIKAS

RDGRVADYAKEFGLVYLEGQQPWSLPVDIALPCATQNELDVDAAHQLI

ANGVKAVAEGANMPTTIEATELFQQAGVLFAPGKAANAGGATCG

LEMAQNAARLGWKAEKVDARLHHIMLDIHHACVEHGGEGEQTNYVQGAN

IAGFVKVADAMLAQGVI (SEQ ID NO: 3)

TABLE 4

Mutant Glutamate Dehydrogenase-2 (GDH2)

MDQTYSLESFLNHVQKRDPNQTEFAQAVREVMTTLWPFLEQNPKYRQMS

LLERLVEPERVIQFRVVWVDDRNQIQVNRAWRVQFSSAIGPYVGGMRF

HPSVNLSILKFLGFEQTFKNALTTLPMGGGKGGSDFDPKGKSEGEVMRF

CQALMTELYRHLGADTDVPAGDIGVGGREVGFMAGMMKKLSNNTACVFS

TABLE 4 -continued

Mutant Glutamate Dehydrogenase-2 (GDH2)

GKGLSFGGSLIRPEATGYGLVYFTEAMLKRHGMFEGMRVSVSGSGNVA

QYAIEKAMEFGARVITASDSSGTVVDESGFTKEKLARLIEIKASRDGRV

ADYAKEFGLVYLEGQQPWSLPVDIALPCATQNELDVDAAHQLIANGVKA

VAEGANMPTTIEATELFQQAGVLFAPGKAANAGGVATSGLEMAQNAARL

GWKAEKVDARLHHIMLDIHHACVEHGGEGEQTNYVQGANIAGFVKVADA

MLAQGVI (SEQ ID NO: 4)

TABLE 5

Inner Membrane Transporter rhtA Polypeptide

LOCUS: YP_003498628 295 aa linear BCT 19 Mar. 2010
DEFINITION: Inner membrane transporter rhtA
[*Escherichia coli* O55:H7 str. CB9615].
ACCESSION: YP_003498628
VERSION: YP_003498628.1 GI:291281810
DBLINK Project: 46655
DBSOURCE REFSEQ: accession NC_013941.1
SOURCE: *Escherichia coli* O55:H7 str. CB9615
ORGANISM: *Escherichia coli* O55:H7 str. CB9615
MPGSLRKMPVWLPIVILLVAMASIQGGASLAKSLFPLVGAPGVTALRLA

LGTLILIAFFKPWRLRFAKEQRLPLLFYGVSLGGMNYLFYLSIQTVPLG

IAVALEFTGPLAVALFSSRRPVDFVWVVLAVLGLWFLLPLGQDVSHVDL

TGCALALGAGACWAIYILSGQRAGAEHGPATVAIGSLIAALIFVPIGAL

QAGEALWHWSVIPLGLAVAILSTALPYSLEMIALTRLPTRTFGTLMSME

PALAAVSGMIFLGETLTPIQLLALGAIIAASMGSTLTVRKESKIKELDI

N (SEQ ID NO: 5)

TABLE 6

Threonine Dehydratase Polypeptide [*Escherichia coli*]

LOCUS: ACI77715 329 aa linear BCT 08 Jun. 2009
DEFINITION: threonine dehydratase [*Escherichia coli*].
ACCESSION: ACI77715
VERSION: ACI77715.1 GI:209758806
DBSOURCE: accession EU895154.1
SOURCE: *Escherichia coli*
ORGANISM: *Escherichia coli*
MHITYDLPVAIDDIIEAKQRLAGRIYKTGMPRSNYFSERCKGEIFLKFEN

MQRTGSFKIRGAFNKLSSLTDAEKRKGVVACSAGNHAQGVSLSCAMLGID

GKVVMPKGAPKSKVAATCDYSAEVVLHGDNFNDTIAKVSEIVEMEGRIFI

PPYDDPKVIAGQGTIGLEIMEDLYDVDNVIVPIGGGGLIAGIAVAIKSIN

PTIRVIGVQSENVHGMAASFHSGEITTHRTTGTLADGCDVSRPGNLTYEI

VRELVDDIVLVSEDEIRNSMIALIQRNKVVTEGAGALACAALLSGKLDQY

IQNRKTVSIISGGNIDLSRVSQITGFVDA (SEQ ID NO: 6)

TABLE 7

Threonine Dehydratase polypeptide
[*Bacillus subtilis*]

LOCUS: AAA96639 422 aa linear BCT 14 Dec. 2001
DEFINITION: threonine dehydratase [*Bacillus subtilis* subsp. *subtilis* str. 168].
ACCESSION: AAA96639
VERSION: AAA96639.1 GI:1256645
DBSOURCE: locus BACYACA accession L77246.1
SOURCE: *Bacillus subtilis* subsp. *subtilis* str. 168
ORGANISM: *Bacillus subtilis* subsp. *subtilis* str. 168

MKPLLKENSLIQVKDILKAHQNVKDVVIHTPLQRNDRLSERYECNIYLKR

EDLQVVRSFKLRGAYHKMKQLSSEQTENGVVCASAGNHAQGVAFSCKHLG

IHGKIFMPSTTPRQKVSQVELFGKGFIDIILTGDTFDDAYKSAAECCEAE

TABLE 7 -continued

Threonine Dehydratase polypeptide
[*Bacillus subtilis*]

SRTFIHPFDDPDVMAGQGTLAVEILNDIDTEPHFLFASVGGGGLLSGVGT

YLKNVSPDTKVIAVEPAGAASYFESNKAGHVVTLDKIDKFVDGAAVIKKI

GEETFRTLETVVDDILLVPEGKVCTSILELYNECAVVAEPAGALSVAALD

LYKDQIKGKNVVCVVSGGNNDIGRNIQEMKERSLIFEGLQHYFIVNFPQR

AGALREFLDEVLGPNDDITRFEYTKKNNKSNGPALVGIELQNKADYGPLI

ERMNKKPFHYVEVNKDEDLFHLLI (SEQ ID NO: 7)

---

The invention claimed is:

1. A composition of matter comprising a mutant glutamate dehydrogenase polypeptide having enzymatic activity to convert 2-ketobutyrate to L-homoalanine and comprising an amino acid sequence having at least 95% amino acid sequence identity to the amino acid sequence of SEQ ID NO: 1, wherein the amino acid residue corresponding to position K92 of SEQ ID NO: 1 is mutated to L or V and the amino acid residue corresponding to position T195 of SEQ ID NO: 1 is mutated to A or S in the mutant glutamate dehydrogenase polypeptide.

2. The composition of claim 1, wherein the mutant glutamate dehydrogenase polypeptide is further modified by 2-10 substitution, deletion or insertion mutations as compared to the amino acid sequence of SEQ ID NO: 1.

3. The composition of claim 2, wherein the mutant glutamate dehydrogenase polypeptide includes the amino acid substitution mutation K92L, K92V, T195A, V377A or S380C.

4. The composition of claim 1, further comprising an *Escherichia coli* or *Corynebacterium glutamicum* microorganism.

5. The composition of claim 4, wherein the *Escherichia coli* or *Corynebacterium glutamicum* microorganism comprises an expression vector comprising a polynucleotide encoding said mutant glutamate dehydrogenase polypeptide.

6. The composition of claim 5, wherein when cultured in a nutrient medium, the *Escherichia coli* microorganism produces at least 2, 3, 4, 5, 6, 7 or 8 g/L threonine from 30 g/L glucose in the nutrient medium.

7. The composition of claim 5, wherein the *Escherichia coli* microorganism further comprises a deletion of a rhtA gene.

8. The composition of claim 5, wherein the *Escherichia coli* microorganism further comprises an expression vector comprising a polynucleotide encoding a polypeptide having threonine dehydratase activity and comprising an amino acid sequence having at least 95% amino acid sequence identity to the amino acid sequence of SEQ ID NO: 6 or SEQ ID NO: 7.

9. The composition of claim 6, wherein the *Escherichia coli* microorganism synthesizes L-homoalanine at a concentration of at least 0.5 g/L in the nutrient medium.

10. A composition of matter comprising:
a mutant glutamate dehydrogenase polypeptide having enzymatic activity to convert 2-ketobutyrate to L-homoalanine and comprising an amino acid sequence having at least 95% amino acid sequence identity to the amino acid sequence of SEQ ID NO: 1, wherein the amino acid residue corresponding to position K92 of SEQ ID NO: 1 is mutated to L or V and the amino acid residue corresponding to position T195 of SEQ ID NO: 1 is mutated to A or S in the mutant glutamate dehydrogenase polypeptide, and further wherein the amino acid residue corresponding to position V377 of SEQ ID NO: 1 is mutated to A or the amino acid residue corresponding to position 5380 of SEQ ID NO: 1 is mutated to C in the mutant glutamate dehydrogenase polypeptide; and
L-homoalanine.

11. The composition of claim 10, further comprising a nutrient medium, wherein the nutrient medium comprises M9, LB, F1 or TB medium, wherein the nutrient medium comprises the L-homoalanine, and wherein the concentration of L-homoalanine in the nutrient medium is at least 0.5 g/L.

12. The composition of claim 10, wherein the mutant glutamate dehydrogenase polypeptide has a specificity constant $k_{cat}/K_m$ for 2-ketobutyrate that is greater than its specificity constant $k_{cat}/K_m$ for 2-ketoglutarate.

13. The composition of claim 10, further comprising an *Escherichia coli* or *Corynebacterium glutamicum* microorganism.

14. The composition of claim 13, wherein the *Escherichia coli* or *Corynebacterium glutamicum* microorganism comprises an expression vector comprising a polynucleotide encoding said mutant glutamate dehydrogenase polypeptide.

15. The composition of claim 14, wherein when cultured in a nutrient medium, the *Escherichia coli* microorganism produces at least 2, 3, 4, 5, 6, 7 or 8 g/L threonine from 30 g/L glucose in the nutrient medium.

16. The composition of claim 14, wherein the *Escherichia coli* microorganism further comprises a deletion of a rhtA gene.

17. The composition of claim 14, wherein the *Escherichia coli* microorganism further comprises an expression vector comprising a polynucleotide encoding a polypeptide having threonine dehydratase activity and comprising an amino acid sequence having at least 95% amino acid sequence identity to the amino acid sequence of SEQ ID NO: 6 or SEQ ID NO: 7.

18. The composition of claim 10, further comprising a nutrient medium comprising M9, LB, F1 or TB medium.

19. A kit for synthesizing L-homoalanine, the kit comprising:
(a) an expression vector encoding a mutant glutamate dehydrogenase polypeptide having enzymatic activity to convert 2-ketobutyrate to L-homoalanine and comprising an amino acid sequence having at least 95% amino acid sequence identity to the amino acid sequence of SEQ ID NO: 1, and wherein the amino acid residue corresponding to position K92 of SEQ ID NO: 1 is mutated to L or V and the amino acid residue corresponding to position T195 of SEQ ID NO: 1 is mutated to A or S in the mutant dehydrogenase polypeptide, and further wherein the amino acid residue corresponding to position V377 of SEQ ID NO: 1 is mutated to A or the amino acid residue corresponding to position 5380 of SEQ ID NO: 1 is mutated to C in the mutant glutamate dehydrogenase polypeptide; and
(b) a container for the expression vector of (a).

20. The kit of claim 19 further comprising:
an expression vector comprising a polynucleotide encoding a polypeptide having threonine dehydratase activity and comprising an amino acid sequence having at least 95% amino acid sequence identity to the amino acid sequence of SEQ ID NO: 6 or SEQ ID NO: 7; and/or
an *Escherichia coli* microorganism, wherein the *Escherichia coli* microorganism comprises a deletion of a rhtA gene.

* * * * *

SEQUENCE LISTING

<160> NUMBER OF SEQ ID NOS: 32

<210> SEQ ID NO 1
<211> LENGTH: 447
<212> TYPE: PRT
<213> ORGANISM: Escherichia coli

<400> SEQUENCE: 1

```
Met Asp Gln Thr Tyr Ser Leu Glu Ser Phe Leu Asn His Val Gln Lys
 1               5                  10                  15

Arg Asp Pro Asn Gln Thr Glu Phe Ala Gln Ala Val Arg Glu Val Met
            20                  25                  30

Thr Thr Leu Trp Pro Phe Leu Glu Gln Asn Pro Lys Tyr Arg Gln Met
        35                  40                  45

Ser Leu Leu Glu Arg Leu Val Gly Pro Glu Arg Val Ile Gln Phe Arg
    50                  55                  60

Val Val Trp Val Asp Asp Arg Asn Gln Ile Gln Val Asn Arg Ala Trp
65                  70                  75                  80

Arg Val Gln Phe Ser Ser Ala Ile Gly Pro Tyr Lys Gly Gly Met Arg
                85                  90                  95

Phe His Pro Ser Val Asn Leu Ser Ile Leu Lys Phe Leu Gly Phe Glu
            100                 105                 110

Gln Thr Phe Lys Asn Ala Leu Thr Thr Leu Pro Met Gly Gly Gly Lys
        115                 120                 125

Gly Gly Ser Asp Phe Asp Pro Lys Gly Lys Ser Glu Gly Glu Val Met
    130                 135                 140

Arg Phe Cys Gln Ala Leu Met Thr Glu Leu Tyr Arg His Leu Gly Ala
145                 150                 155                 160

Asp Thr Asp Val Pro Ala Gly Asp Ile Gly Val Gly Gly Arg Glu Val
                165                 170                 175

Gly Phe Met Ala Gly Met Met Lys Lys Leu Ser Asn Asn Thr Ala Cys
            180                 185                 190

Val Phe Thr Gly Lys Gly Leu Ser Phe Gly Gly Ser Leu Ile Arg Pro
        195                 200                 205

Glu Ala Thr Gly Tyr Gly Leu Val Tyr Phe Thr Glu Ala Met Leu Lys
    210                 215                 220

Arg His Gly Met Gly Phe Glu Gly Met Arg Val Ser Val Ser Gly Ser
225                 230                 235                 240

Gly Asn Val Ala Gln Tyr Ala Ile Glu Lys Ala Met Glu Phe Gly Ala
                245                 250                 255
```

```
Arg Val Ile Thr Ala Ser Asp Ser Ser Gly Thr Val Val Asp Glu Ser
                260                 265                 270
Gly Phe Thr Lys Glu Lys Leu Ala Arg Leu Ile Glu Ile Lys Ala Ser
            275                 280                 285
Arg Asp Gly Arg Val Ala Asp Tyr Ala Lys Glu Phe Gly Leu Val Tyr
        290                 295                 300
Leu Glu Gly Gln Gln Pro Trp Ser Leu Pro Val Asp Ile Ala Leu Pro
305                 310                 315                 320
Cys Ala Thr Gln Asn Glu Leu Asp Val Asp Ala Ala His Gln Leu Ile
                325                 330                 335
Ala Asn Gly Val Lys Ala Val Ala Glu Gly Ala Asn Met Pro Thr Thr
            340                 345                 350
Ile Glu Ala Thr Glu Leu Phe Gln Gln Ala Gly Val Leu Phe Ala Pro
        355                 360                 365
Gly Lys Ala Ala Asn Ala Gly Gly Val Ala Thr Ser Gly Leu Glu Met
        370                 375                 380
Ala Gln Asn Ala Ala Arg Leu Gly Trp Lys Ala Glu Lys Val Asp Ala
385                 390                 395                 400
Arg Leu His His Ile Met Leu Asp Ile His His Ala Cys Val Glu His
                405                 410                 415
Gly Gly Glu Gly Glu Gln Thr Asn Tyr Val Gln Gly Ala Asn Ile Ala
            420                 425                 430
Gly Phe Val Lys Val Ala Asp Ala Met Leu Ala Gln Gly Val Ile
        435                 440                 445

<210> SEQ ID NO 2
<211> LENGTH: 1779
<212> TYPE: DNA
<213> ORGANISM: Escherichia coli

<400> SEQUENCE: 2
ccgggtggca aactttagc gtctgaggtt atcgcatttg gttatgagat tactctcgtt    60
attaatttgc tttcctgggt catttttttc ttgcttaccg tcacattctt gatggtatag   120
tcgaaaactg caaaagcaca tgacataaac aacataagca caatcgtatt aatatataag   180
ggttttatat ctatggatca gacatattct ctggagtcat tcctcaacca tgtccaaaag   240
cgcgacccga atcaaaccga gttcgcgcaa gccgttcgtg aagtaatgac cacactctgg   300
ccttttcttg aacaaaatcc aaaatatcgc cagatgtcat tactggagcg tctggttgaa   360
ccggagcgcg tgatccagtt tcgcgtggta tgggttgatg atcgcaacca gatacaggtc   420
aaccgtgcat ggcgtgtgca gttcagctct gccatcggcc cgtacaaagg cggtatgcgc   480
ttccatccgt cagttaacct ttccattctc aaattcctcg gctttgaaca aaccttcaaa   540
aatgccctga ctactctgcc gatgggcggt ggtaaaggcg gcagcgattt cgatccgaaa   600
ggaaaaagcg aaggtgaagt gatgcgtttt tgccaggcgc tgatgactga actgtatcgc   660
cacctgggcg cggataccga cgttccggca ggtgatatcg gggttggtgg tcgtgaagtc   720
ggctttatgg cggggatgat gaaaaagctc tccaacaata ccgcctgcgt cttcaccggt   780
aagggccttt catttggcgg cagtcttatt cgcccggaag ctaccggcta cggtctggtt   840
tatttcacag aagcaatgct aaaacgccac ggtatgggtt ttgaagggat gcgcgtttcc   900
gtttctggct ccggcaacgt cgcccagtac gctatcgaaa aagcgatgga atttggtgct   960
cgtgtgatca ctgcgtcaga ctccagcggc actgtagttg atgaaagcgg attcacgaaa  1020
```

-continued

```
gagaaactgg cacgtcttat cgaaatcaaa gccagccgcg atggtcgagt ggcagattac    1080
gccaaagaat ttggtctggt ctatctcgaa ggccaacagc cgtggtctct accggttgat    1140
atcgccctgc cttgcgccac ccagaatgaa ctggatgttg acgccgcgca tcagcttatc    1200
gctaatggcg ttaaagccgt cgccgaaggg gcaaatatgc cgaccaccat cgaagcgact    1260
gaactgttcc agcaggcagg cgtactattt gcaccgggta agcggctaa tgctggtggc    1320 gtcgctacat cgggcctgga atggcacaa acgctgcgc gcctgggctg aaagccgag    1380 aaagttgacg cacgtttgca tcacatcatg ctggatatcc accatgcctg tgttgagcat    1440
ggtggtgaag gtgagcaaac caactacgtg cagggcgcga acattgccgg ttttgtgaag    1500
gttgccgatg cgatgctggc gcagggtgtg atttaagttg taaatgcctg atggcgctac    1560
gcttatcagg cctacaaatg gcacaattc attgcagtta cgctctaatg taggccgggc    1620
aagcgcagcg ccccggcaa aatttcaggc gtttatgagt atttaacgga tgatgctccc    1680
cacggaacat ttcttatggg ccaacggcat ttcttactgt agtgctccca aaactgcttg    1740
tcgtaacgat aacacgcttc aagttcagca tccgttaac                           1779
```

<210> SEQ ID NO 3
<211> LENGTH: 447
<212> TYPE: PRT
<213> ORGANISM: Escherichia coli

<400> SEQUENCE: 3

```
Met Asp Gln Thr Tyr Ser Leu Glu Ser Phe Leu Asn His Val Gln Lys
  1               5                  10                  15

Arg Asp Pro Asn Gln Thr Glu Phe Ala Gln Ala Val Arg Glu Val Met
             20                  25                  30

Thr Thr Leu Trp Pro Phe Leu Glu Gln Asn Pro Lys Tyr Arg Gln Met
         35                  40                  45

Ser Leu Leu Glu Arg Leu Val Glu Pro Glu Arg Val Ile Gln Phe Arg
     50                  55                  60

Val Val Trp Val Asp Asp Arg Asn Gln Ile Gln Val Asn Arg Ala Trp
 65                  70                  75                  80

Arg Val Gln Phe Ser Ser Ala Ile Gly Pro Tyr Leu Gly Gly Met Arg
                 85                  90                  95

Phe His Pro Ser Val Asn Leu Ser Ile Leu Lys Phe Leu Gly Phe Glu
            100                 105                 110

Gln Thr Phe Lys Asn Ala Leu Thr Thr Leu Pro Met Gly Gly Gly Lys
        115                 120                 125

Gly Gly Ser Asp Phe Asp Pro Lys Gly Lys Ser Glu Gly Glu Val Met
    130                 135                 140

Arg Phe Cys Gln Ala Leu Met Thr Glu Leu Tyr Arg His Leu Gly Ala
145                 150                 155                 160

Asp Thr Asp Val Pro Ala Gly Asp Ile Gly Val Gly Gly Arg Glu Val
                165                 170                 175

Gly Phe Met Ala Gly Met Met Lys Lys Leu Ser Asn Asn Thr Ala Cys
            180                 185                 190

Val Phe Ala Gly Lys Gly Leu Ser Phe Gly Gly Ser Leu Ile Arg Pro
        195                 200                 205

Glu Ala Thr Gly Tyr Gly Leu Val Tyr Phe Thr Glu Ala Met Leu Lys
    210                 215                 220

Arg His Gly Met Gly Phe Glu Gly Met Arg Val Ser Val Ser Gly Ser
225                 230                 235                 240
```

-continued

```
Gly Asn Val Ala Gln Tyr Ala Ile Glu Lys Ala Met Glu Phe Gly Ala
                245                 250                 255

Arg Val Ile Thr Ala Ser Asp Ser Ser Gly Thr Val Val Asp Glu Ser
            260                 265                 270

Gly Phe Thr Lys Glu Lys Leu Ala Arg Leu Ile Glu Ile Lys Ala Ser
        275                 280                 285

Arg Asp Gly Arg Val Ala Asp Tyr Ala Lys Glu Phe Gly Leu Val Tyr
    290                 295                 300

Leu Glu Gly Gln Gln Pro Trp Ser Leu Pro Val Asp Ile Ala Leu Pro
305                 310                 315                 320

Cys Ala Thr Gln Asn Glu Leu Asp Val Asp Ala Ala His Gln Leu Ile
                325                 330                 335

Ala Asn Gly Val Lys Ala Val Ala Glu Gly Ala Asn Met Pro Thr Thr
            340                 345                 350

Ile Glu Ala Thr Glu Leu Phe Gln Gln Ala Gly Val Leu Phe Ala Pro
        355                 360                 365

Gly Lys Ala Ala Asn Ala Gly Gly Ala Ala Thr Cys Gly Leu Glu Met
    370                 375                 380

Ala Gln Asn Ala Ala Arg Leu Gly Trp Lys Ala Glu Lys Val Asp Ala
385                 390                 395                 400

Arg Leu His His Ile Met Leu Asp Ile His His Ala Cys Val Glu His
                405                 410                 415

Gly Gly Glu Gly Glu Gln Thr Asn Tyr Val Gln Gly Ala Asn Ile Ala
            420                 425                 430

Gly Phe Val Lys Val Ala Asp Ala Met Leu Ala Gln Gly Val Ile
        435                 440                 445

<210> SEQ ID NO 4
<211> LENGTH: 447
<212> TYPE: PRT
<213> ORGANISM: Escherichia coli

<400> SEQUENCE: 4

Met Asp Gln Thr Tyr Ser Leu Glu Ser Phe Leu Asn His Val Gln Lys
1               5                   10                  15

Arg Asp Pro Asn Gln Thr Glu Phe Ala Gln Ala Val Arg Glu Val Met
                20                  25                  30

Thr Thr Leu Trp Pro Phe Leu Glu Gln Asn Pro Lys Tyr Arg Gln Met
            35                  40                  45

Ser Leu Leu Glu Arg Leu Val Glu Pro Glu Arg Val Ile Gln Phe Arg
        50                  55                  60

Val Val Trp Val Asp Asp Arg Asn Gln Ile Gln Val Asn Arg Ala Trp
65                  70                  75                  80

Arg Val Gln Phe Ser Ser Ala Ile Gly Pro Tyr Val Gly Gly Met Arg
                85                  90                  95

Phe His Pro Ser Val Asn Leu Ser Ile Leu Lys Phe Leu Gly Phe Glu
            100                 105                 110

Gln Thr Phe Lys Asn Ala Leu Thr Thr Leu Pro Met Gly Gly Gly Lys
        115                 120                 125

Gly Gly Ser Asp Phe Asp Pro Lys Gly Lys Ser Glu Gly Glu Val Met
    130                 135                 140

Arg Phe Cys Gln Ala Leu Met Thr Glu Leu Tyr Arg His Leu Gly Ala
145                 150                 155                 160

Asp Thr Asp Val Pro Ala Gly Asp Ile Gly Val Gly Gly Arg Glu Val
                165                 170                 175
```

Gly Phe Met Ala Gly Met Met Lys Lys Leu Ser Asn Asn Thr Ala Cys
            180                 185                 190

Val Phe Ser Gly Lys Gly Leu Ser Phe Gly Gly Ser Leu Ile Arg Pro
            195                 200             205

Glu Ala Thr Gly Tyr Gly Leu Val Tyr Phe Thr Glu Ala Met Leu Lys
            210                 215                 220

Arg His Gly Met Gly Phe Glu Gly Met Arg Val Ser Val Ser Gly Ser
225                 230                 235                 240

Gly Asn Val Ala Gln Tyr Ala Ile Glu Lys Ala Met Glu Phe Gly Ala
                245                 250                 255

Arg Val Ile Thr Ala Ser Asp Ser Ser Gly Thr Val Val Asp Glu Ser
            260                 265                 270

Gly Phe Thr Lys Glu Lys Leu Ala Arg Leu Ile Glu Ile Lys Ala Ser
            275                 280                 285

Arg Asp Gly Arg Val Ala Asp Tyr Ala Lys Glu Phe Gly Leu Val Tyr
    290                 295                 300

Leu Glu Gly Gln Gln Pro Trp Ser Leu Pro Val Asp Ile Ala Leu Pro
305                 310                 315                 320

Cys Ala Thr Gln Asn Glu Leu Asp Val Asp Ala Ala His Gln Leu Ile
                325                 330                 335

Ala Asn Gly Val Lys Ala Val Ala Glu Gly Ala Asn Met Pro Thr Thr
            340                 345                 350

Ile Glu Ala Thr Glu Leu Phe Gln Gln Ala Gly Val Leu Phe Ala Pro
            355                 360                 365

Gly Lys Ala Ala Asn Ala Gly Val Ala Thr Ser Gly Leu Glu Met
            370                 375                 380

Ala Gln Asn Ala Ala Arg Leu Gly Trp Lys Ala Glu Lys Val Asp Ala
385                 390                 395                 400

Arg Leu His His Ile Met Leu Asp Ile His His Ala Cys Val Glu His
                405                 410                 415

Gly Gly Glu Gly Glu Gln Thr Asn Tyr Val Gln Gly Ala Asn Ile Ala
            420                 425                 430

Gly Phe Val Lys Val Ala Asp Ala Met Leu Ala Gln Gly Val Ile
            435                 440                 445

<210> SEQ ID NO 5
<211> LENGTH: 295
<212> TYPE: PRT
<213> ORGANISM: Escherichia coli

<400> SEQUENCE: 5

Met Pro Gly Ser Leu Arg Lys Met Pro Val Trp Leu Pro Ile Val Ile
1               5                   10                  15

Leu Leu Val Ala Met Ala Ser Ile Gln Gly Gly Ala Ser Leu Ala Lys
            20                  25                  30

Ser Leu Phe Pro Leu Val Gly Ala Pro Gly Val Thr Ala Leu Arg Leu
        35                  40                  45

Ala Leu Gly Thr Leu Ile Leu Ile Ala Phe Phe Lys Pro Trp Arg Leu
    50                  55                  60

Arg Phe Ala Lys Glu Gln Arg Leu Pro Leu Leu Phe Tyr Gly Val Ser
65                  70                  75                  80

Leu Gly Gly Met Asn Tyr Leu Phe Tyr Leu Ser Ile Gln Thr Val Pro
                85                  90                  95

Leu Gly Ile Ala Val Ala Leu Glu Phe Thr Gly Pro Leu Ala Val Ala

```
            100                 105                 110
Leu Phe Ser Ser Arg Arg Pro Val Asp Phe Val Trp Val Leu Ala
        115                 120                 125
Val Leu Gly Leu Trp Phe Leu Pro Leu Gly Gln Asp Val Ser His
        130                 135                 140
Val Asp Leu Thr Gly Cys Ala Leu Ala Leu Gly Ala Gly Ala Cys Trp
145                 150                 155                 160
Ala Ile Tyr Ile Leu Ser Gly Gln Arg Ala Gly Ala Glu His Gly Pro
                165                 170                 175
Ala Thr Val Ala Ile Gly Ser Leu Ile Ala Ala Leu Ile Phe Val Pro
                180                 185                 190
Ile Gly Ala Leu Gln Ala Gly Glu Ala Leu Trp His Trp Ser Val Ile
        195                 200                 205
Pro Leu Gly Leu Ala Val Ala Ile Leu Ser Thr Ala Leu Pro Tyr Ser
        210                 215                 220
Leu Glu Met Ile Ala Leu Thr Arg Leu Pro Thr Arg Thr Phe Gly Thr
225                 230                 235                 240
Leu Met Ser Met Glu Pro Ala Leu Ala Ala Val Ser Gly Met Ile Phe
                245                 250                 255
Leu Gly Glu Thr Leu Thr Pro Ile Gln Leu Leu Ala Leu Gly Ala Ile
                260                 265                 270
Ile Ala Ala Ser Met Gly Ser Thr Leu Thr Val Arg Lys Glu Ser Lys
        275                 280                 285
Ile Lys Glu Leu Asp Ile Asn
        290                 295

<210> SEQ ID NO 6
<211> LENGTH: 329
<212> TYPE: PRT
<213> ORGANISM: Escherichia coli

<400> SEQUENCE: 6

Met His Ile Thr Tyr Asp Leu Pro Val Ala Ile Asp Ile Ile Glu
1               5                   10                  15
Ala Lys Gln Arg Leu Ala Gly Arg Ile Tyr Lys Thr Gly Met Pro Arg
                20                  25                  30
Ser Asn Tyr Phe Ser Glu Arg Cys Lys Gly Glu Ile Phe Leu Lys Phe
        35                  40                  45
Glu Asn Met Gln Arg Thr Gly Ser Phe Lys Ile Arg Gly Ala Phe Asn
    50                  55                  60
Lys Leu Ser Ser Leu Thr Asp Ala Glu Lys Arg Lys Gly Val Val Ala
65                  70                  75                  80
Cys Ser Ala Gly Asn His Ala Gln Gly Val Ser Leu Ser Cys Ala Met
                85                  90                  95
Leu Gly Ile Asp Gly Lys Val Val Met Pro Lys Gly Ala Pro Lys Ser
                100                 105                 110
Lys Val Ala Ala Thr Cys Asp Tyr Ser Ala Glu Val Val Leu His Gly
        115                 120                 125
Asp Asn Phe Asn Asp Thr Ile Ala Lys Val Ser Glu Ile Val Glu Met
        130                 135                 140
Glu Gly Arg Ile Phe Ile Pro Pro Tyr Asp Asp Pro Lys Val Ile Ala
145                 150                 155                 160
Gly Gln Gly Thr Ile Gly Leu Glu Ile Met Glu Asp Leu Tyr Asp Val
                165                 170                 175
```

```
Asp Asn Val Ile Val Pro Ile Gly Gly Gly Leu Ile Ala Gly Ile
            180                 185                 190

Ala Val Ala Ile Lys Ser Ile Asn Pro Thr Ile Arg Val Ile Gly Val
        195                 200                 205

Gln Ser Glu Asn Val His Gly Met Ala Ala Ser Phe His Ser Gly Glu
    210                 215                 220

Ile Thr Thr His Arg Thr Thr Gly Thr Leu Ala Asp Gly Cys Asp Val
225                 230                 235                 240

Ser Arg Pro Gly Asn Leu Thr Tyr Glu Ile Val Arg Glu Leu Val Asp
                245                 250                 255

Asp Ile Val Leu Val Ser Glu Asp Glu Ile Arg Asn Ser Met Ile Ala
            260                 265                 270

Leu Ile Gln Arg Asn Lys Val Val Thr Glu Gly Ala Gly Ala Leu Ala
        275                 280                 285

Cys Ala Ala Leu Leu Ser Gly Lys Leu Asp Gln Tyr Ile Gln Asn Arg
    290                 295                 300

Lys Thr Val Ser Ile Ile Ser Gly Gly Asn Ile Asp Leu Ser Arg Val
305                 310                 315                 320

Ser Gln Ile Thr Gly Phe Val Asp Ala
                325

<210> SEQ ID NO 7
<211> LENGTH: 422
<212> TYPE: PRT
<213> ORGANISM: Bacillus subtilis

<400> SEQUENCE: 7

Met Lys Pro Leu Leu Lys Glu Asn Ser Leu Ile Gln Val Lys Asp Ile
1               5                   10                  15

Leu Lys Ala His Gln Asn Val Lys Asp Val Val Ile His Thr Pro Leu
            20                  25                  30

Gln Arg Asn Asp Arg Leu Ser Glu Arg Tyr Glu Cys Asn Ile Tyr Leu
        35                  40                  45

Lys Arg Glu Asp Leu Gln Val Val Arg Ser Phe Lys Leu Arg Gly Ala
    50                  55                  60

Tyr His Lys Met Lys Gln Leu Ser Ser Glu Gln Thr Glu Asn Gly Val
65                  70                  75                  80

Val Cys Ala Ser Ala Gly Asn His Ala Gln Gly Val Ala Phe Ser Cys
                85                  90                  95

Lys His Leu Gly Ile His Gly Lys Ile Phe Met Pro Ser Thr Thr Pro
            100                 105                 110

Arg Gln Lys Val Ser Gln Val Glu Leu Phe Gly Lys Gly Phe Ile Asp
        115                 120                 125

Ile Ile Leu Thr Gly Asp Thr Phe Asp Asp Ala Tyr Lys Ser Ala Ala
    130                 135                 140

Glu Cys Cys Glu Ala Glu Ser Arg Thr Phe Ile His Pro Phe Asp Asp
145                 150                 155                 160

Pro Asp Val Met Ala Gly Gln Gly Thr Leu Ala Val Glu Ile Leu Asn
                165                 170                 175

Asp Ile Asp Thr Glu Pro His Phe Leu Phe Ala Ser Val Gly Gly Gly
            180                 185                 190

Gly Leu Leu Ser Gly Val Gly Thr Tyr Leu Lys Asn Val Ser Pro Asp
        195                 200                 205

Thr Lys Val Ile Ala Val Glu Pro Ala Gly Ala Ala Ser Tyr Phe Glu
    210                 215                 220
```

```
Ser Asn Lys Ala Gly His Val Val Thr Leu Asp Lys Ile Asp Lys Phe
225                 230                 235                 240

Val Asp Gly Ala Ala Val Lys Lys Ile Gly Glu Glu Thr Phe Arg Thr
            245                 250                 255

Leu Glu Thr Val Val Asp Asp Ile Leu Leu Val Pro Gly Lys Val
                260                 265                 270

Cys Thr Ser Ile Leu Glu Leu Tyr Asn Glu Cys Ala Val Val Ala Glu
            275                 280                 285

Pro Ala Gly Ala Leu Ser Val Ala Ala Leu Asp Leu Tyr Lys Asp Gln
            290                 295                 300

Ile Lys Gly Lys Asn Val Val Cys Val Val Ser Gly Gly Asn Asn Asp
305                 310                 315                 320

Ile Gly Arg Met Gln Glu Met Lys Glu Arg Ser Leu Ile Phe Glu Gly
                325                 330                 335

Leu Gln His Tyr Phe Ile Val Asn Phe Pro Gln Arg Ala Gly Ala Leu
            340                 345                 350

Arg Glu Phe Leu Asp Glu Val Leu Gly Pro Asn Asp Asp Ile Thr Arg
            355                 360                 365

Phe Glu Tyr Thr Lys Lys Asn Asn Lys Ser Asn Gly Pro Ala Leu Val
            370                 375                 380

Gly Ile Glu Leu Gln Asn Lys Ala Asp Tyr Gly Pro Leu Ile Glu Arg
385                 390                 395                 400

Met Asn Lys Lys Pro Phe His Tyr Val Glu Val Asn Lys Asp Glu Asp
                405                 410                 415

Leu Phe His Leu Leu Ile
            420

<210> SEQ ID NO 8
<211> LENGTH: 41
<212> TYPE: DNA
<213> ORGANISM: Artificial Sequence
<220> FEATURE:
<223> OTHER INFORMATION: primer

<400> SEQUENCE: 8
gcatacggta ccatgaccac gaagaaagct gattacattt g                 41

<210> SEQ ID NO 9
<211> LENGTH: 43
<212> TYPE: DNA
<213> ORGANISM: Artificial Sequence
<220> FEATURE:
<223> OTHER INFORMATION: primer

<400> SEQUENCE: 9
gcatactcta gattattgat taacttgatc taaccagccc cat               43

<210> SEQ ID NO 10
<211> LENGTH: 35
<212> TYPE: DNA
<213> ORGANISM: Artificial Sequence
<220> FEATURE:
<223> OTHER INFORMATION: primer

<400> SEQUENCE: 10
gcatacggta ccatgaccga tgtatccgac ggcgt                        35

<210> SEQ ID NO 11
<211> LENGTH: 37
```

```
<212> TYPE: DNA
<213> ORGANISM: Artificial Sequence
<220> FEATURE:
<223> OTHER INFORMATION: primer

<400> SEQUENCE: 11
gcatactcta gattagcccc ggcgggcctc cgccatg                                    37

<210> SEQ ID NO 12
<211> LENGTH: 35
<212> TYPE: DNA
<213> ORGANISM: Artificial Sequence
<220> FEATURE:
<223> OTHER INFORMATION: primer

<400> SEQUENCE: 12
gcatacggta ccatgaccga cgtaaacggc gcacc                                      35

<210> SEQ ID NO 13
<211> LENGTH: 40
<212> TYPE: DNA
<213> ORGANISM: Artificial Sequence
<220> FEATURE:
<223> OTHER INFORMATION: primer

<400> SEQUENCE: 13
gcatactcta gattacggcc ggggacgggc ctccgccatc                                 40

<210> SEQ ID NO 14
<211> LENGTH: 35
<212> TYPE: DNA
<213> ORGANISM: Artificial Sequence
<220> FEATURE:
<223> OTHER INFORMATION: primer

<400> SEQUENCE: 14
gcatacggta ccatgaccga cgcgtcccac cccac                                      35

<210> SEQ ID NO 15
<211> LENGTH: 37
<212> TYPE: DNA
<213> ORGANISM: Artificial Sequence
<220> FEATURE:
<223> OTHER INFORMATION: primer

<400> SEQUENCE: 15
gcatactcta gattagacgg tgcgggcctc cgccatg                                    37

<210> SEQ ID NO 16
<211> LENGTH: 42
<212> TYPE: DNA
<213> ORGANISM: Artificial Sequence
<220> FEATURE:
<223> OTHER INFORMATION: primer

<400> SEQUENCE: 16
gcatacggta ccatggatca gacatattct ctggagtcat tc                              42

<210> SEQ ID NO 17
<211> LENGTH: 34
<212> TYPE: DNA
<213> ORGANISM: Artificial Sequence
<220> FEATURE:
<223> OTHER INFORMATION: primer

<400> SEQUENCE: 17
```
gcatactcta gattaaatca caccctgcgc cagc                                    34

<210> SEQ ID NO 18
<211> LENGTH: 44
<212> TYPE: DNA
<213> ORGANISM: Artificial Sequence
<220> FEATURE:
<221> NAME/KEY: misc_feature
<222> LOCATION: (21)...(22)
<223> OTHER INFORMATION: n=a, t, c, or g
<220> FEATURE:
<221> NAME/KEY: misc_feature
<222> LOCATION: (23)...(23)
<223> OTHER INFORMATION: k=g or t
<220> FEATURE:
<223> OTHER INFORMATION: primer

<400> SEQUENCE: 18
gctctgccat cggcccgtac nnkggcggta tgcgcttcca tccg                         44

<210> SEQ ID NO 19
<211> LENGTH: 44
<212> TYPE: DNA
<213> ORGANISM: Artificial Sequence
<220> FEATURE:
<221> NAME/KEY: misc_feature
<222> LOCATION: (22)...(22)
<223> OTHER INFORMATION: m=a or c
<220> FEATURE:
<221> NAME/KEY: misc_feature
<222> LOCATION: (23)...(24)
<223> OTHER INFORMATION: n=a, t, c, or g
<220> FEATURE:
<223> OTHER INFORMATION: primer

<400> SEQUENCE: 19
cggatggaag cgcataccgc cmnngtacgg gccgatggca gagc                         44

<210> SEQ ID NO 20
<211> LENGTH: 45
<212> TYPE: DNA
<213> ORGANISM: Artificial Sequence
<220> FEATURE:
<221> NAME/KEY: misc_feature
<222> LOCATION: (23)...(24)
<223> OTHER INFORMATION: n=a, t, c, or g
<220> FEATURE:
<221> NAME/KEY: misc_feature
<222> LOCATION: (25)...(25)
<223> OTHER INFORMATION: k=g or t
<220> FEATURE:
<223> OTHER INFORMATION: primer

<400> SEQUENCE: 20
caacaatacc gcctgcgtct tcnnkggtaa gggcctttca tttgg                        45

<210> SEQ ID NO 21
<211> LENGTH: 45
<212> TYPE: DNA
<213> ORGANISM: Artificial Sequence
<220> FEATURE:
<221> NAME/KEY: misc_feature
<222> LOCATION: (21)...(21)
<223> OTHER INFORMATION: m=a or c
<220> FEATURE:
<221> NAME/KEY: misc_feature
<222> LOCATION: (22)...(23)
<223> OTHER INFORMATION: n=a, t, c, or g
<220> FEATURE:
<223> OTHER INFORMATION: primer

<400> SEQUENCE: 21

```
ccaaatgaaa ggcccttacc mnngaagacg caggcggtat tgttg              45
```

<210> SEQ ID NO 22
<211> LENGTH: 56
<212> TYPE: DNA
<213> ORGANISM: Artificial Sequence
<220> FEATURE:
<221> NAME/KEY: misc_feature
<222> LOCATION: 24, 25, 33, 34
<223> OTHER INFORMATION: n=a, t, c, or g
<220> FEATURE:
<221> NAME/KEY: misc_feature
<222> LOCATION: 26, 35
<223> OTHER INFORMATION: k=g or t
<220> FEATURE:
<223> OTHER INFORMATION: primer

<400> SEQUENCE: 22

```
gtaaagcggc taatgctggt ggcnnkgcta cannkggcct ggaaatggca caaaac    56
```

<210> SEQ ID NO 23
<211> LENGTH: 56
<212> TYPE: DNA
<213> ORGANISM: Artificial Sequence
<220> FEATURE:
<221> NAME/KEY: misc_feature
<222> LOCATION: 22, 31
<223> OTHER INFORMATION: m=a or c
<220> FEATURE:
<221> NAME/KEY: misc_feature
<222> LOCATION: 23, 24, 32, 33
<223> OTHER INFORMATION: n=a, c, t, or g
<220> FEATURE:
<223> OTHER INFORMATION: primer

<400> SEQUENCE: 23

```
gttttgtgcc atttccaggc cmnntgtagc mnngccacca gcattagccg ctttac    56
```

<210> SEQ ID NO 24
<211> LENGTH: 59
<212> TYPE: DNA
<213> ORGANISM: Artificial Sequence
<220> FEATURE:
<223> OTHER INFORMATION: primer

<400> SEQUENCE: 24

```
gcatacgtcg acaagaggag aaagttacca tggatcagac atattctctg gagtcattc    59
```

<210> SEQ ID NO 25
<211> LENGTH: 40
<212> TYPE: DNA
<213> ORGANISM: Artificial Sequence
<220> FEATURE:
<223> OTHER INFORMATION: primer

<400> SEQUENCE: 25

```
gcatacggta ccatgcatat tacatacgat ctgccggttg                    40
```

<210> SEQ ID NO 26
<211> LENGTH: 39
<212> TYPE: DNA
<213> ORGANISM: Artificial Sequence
<220> FEATURE:
<223> OTHER INFORMATION: primer

<400> SEQUENCE: 26

```
gcatacgtcg acttaagcgt caacgaaacc ggtgatttg                     39
```

```
<210> SEQ ID NO 27
<211> LENGTH: 33
<212> TYPE: DNA
<213> ORGANISM: Artificial Sequence
<220> FEATURE:
<223> OTHER INFORMATION: primer

<400> SEQUENCE: 27
gcatacggta ccatggctga ctcgcaaccc ctg                                    33

<210> SEQ ID NO 28
<211> LENGTH: 35
<212> TYPE: DNA
<213> ORGANISM: Artificial Sequence
<220> FEATURE:
<223> OTHER INFORMATION: primer

<400> SEQUENCE: 28
gcatacgtcg acctaacccg ccaaaaagaa cctga                                  35

<210> SEQ ID NO 29
<211> LENGTH: 42
<212> TYPE: DNA
<213> ORGANISM: Artificial Sequence
<220> FEATURE:
<223> OTHER INFORMATION: primer

<400> SEQUENCE: 29
gcatacggta ccatgaaacc gttgcttaaa gaaaactctc tc                          42

<210> SEQ ID NO 30
<211> LENGTH: 43
<212> TYPE: DNA
<213> ORGANISM: Artificial Sequence
<220> FEATURE:
<223> OTHER INFORMATION: primer

<400> SEQUENCE: 30
gcatacgtcg acttagatta gcaaatggaa caagtcctca tcc                         43

<210> SEQ ID NO 31
<211> LENGTH: 42
<212> TYPE: DNA
<213> ORGANISM: Artificial Sequence
<220> FEATURE:
<223> OTHER INFORMATION: primer

<400> SEQUENCE: 31
gcatacggat ccatggatca gacatattct ctggagtcat tc                          42

<210> SEQ ID NO 32
<211> LENGTH: 34
<212> TYPE: DNA
<213> ORGANISM: Artificial Sequence
<220> FEATURE:
<223> OTHER INFORMATION: primer

<400> SEQUENCE: 32
gcatacggat ccttaaatca caccctgcgc cagc                                   34
```